(12) United States Patent
Behl et al.

(10) Patent No.: US 8,911,450 B2
(45) Date of Patent: Dec. 16, 2014

(54) METHODS AND APPARATUS FOR DEPLOYING URETERAL STENTS

(71) Applicant: Percutaneous Systems, Inc., Palo Alto, CA (US)

(72) Inventors: Robert S. Behl, Monterey, CA (US); Alexander L. Huang, Menlo Park, CA (US); Linh A. Dinh, Irvine, CA (US)

(73) Assignee: Percutaneous Systems, Inc., Palo Alto, CA (US)

( * ) Notice: Subject to any disclaimer, the term of this patent is extended or adjusted under 35 U.S.C. 154(b) by 0 days.

(21) Appl. No.: 13/907,705

(22) Filed: May 31, 2013

(65) Prior Publication Data

US 2013/0267990 A1    Oct. 10, 2013

Related U.S. Application Data

(60) Continuation of application No. 13/073,680, filed on Mar. 28, 2011, which is a division of application No. 11/436,256, filed on May 17, 2006, now Pat. No. 7,972,292, which is a continuation-in-part of application No. PCT/US2005/023988, filed on Jul. 6, 2005, which is a continuation of application No. 10/886,886, filed on Jul. 7, 2004, now Pat. No. 7,462,183.

(51) Int. Cl.
| | |
|---|---|
| *A61B 17/22* | (2006.01) |
| *A61M 29/00* | (2006.01) |
| *A61M 25/01* | (2006.01) |
| *A61M 25/04* | (2006.01) |
| *A61M 27/00* | (2006.01) |

(52) U.S. Cl.
CPC ............ *A61M 29/00* (2013.01); *A61M 25/0102* (2013.01); *A61M 25/04* (2013.01); *A61M 27/008* (2013.01); *A61M 25/0133* (2013.01)
USPC ........................................................ 606/127

(58) Field of Classification Search
USPC ......... 606/110, 113, 114, 127, 128, 192, 200; 623/23.64, 23.66
See application file for complete search history.

(56) References Cited

U.S. PATENT DOCUMENTS

| | | | |
|---|---|---|---|
| 4,030,406 A | 6/1977 | Wander et al. | |
| 4,030,503 A | 6/1977 | Clark, III | |

(Continued)

FOREIGN PATENT DOCUMENTS

| | | |
|---|---|---|
| DE | 10031661 A1 | 1/2002 |
| EP | 605427 B1 | 5/1998 |

(Continued)

OTHER PUBLICATIONS

Bard Urological Division Catalog 1990, PA24, Woven Blasucci Ureteral Catheters, 3 pages.

(Continued)

*Primary Examiner* — Jonathan W Miles
(74) *Attorney, Agent, or Firm* — Wilson Sonsini Goodrich & Rosati

(57) ABSTRACT

A ureteral decompression device comprises a guide member and an anchoring structure. The guide member may be introduced through the urethra and bladder into the ureter so that the anchor structure passes a lodged kidney stone. Once past the stone, the anchor structure can be compacted to anchor the guide member in place. The anchor structure will permit leakage and the guide member will provide a leakage path directly past the stone, thus decompressing the kidney.

11 Claims, 26 Drawing Sheets

(56) References Cited

U.S. PATENT DOCUMENTS

| | | | |
|---|---|---|---|
| 4,046,149 A | 9/1977 | Komiya | |
| 4,262,677 A | 4/1981 | Bader | |
| 4,295,464 A | 10/1981 | Shihata | |
| 4,531,933 A | 7/1985 | Norton et al. | |
| 4,706,671 A | 11/1987 | Weinrib | |
| 4,762,130 A | 8/1988 | Fogarty et al. | |
| 4,807,626 A | 2/1989 | McGirr | |
| 4,813,925 A | 3/1989 | Anderson, Jr. et al. | |
| 4,930,496 A | 6/1990 | Bosley, Jr. | |
| 5,011,488 A | 4/1991 | Ginsburg | |
| 5,078,727 A | 1/1992 | Hannam et al. | |
| 5,135,534 A | 8/1992 | Tulip | |
| 5,192,286 A | 3/1993 | Phan et al. | |
| 5,431,676 A | 7/1995 | Dubrul et al. | |
| 5,454,790 A | 10/1995 | Dubrul | |
| 2,756,752 A | 7/1996 | Scherlis | |
| 5,531,717 A | 7/1996 | Roberto et al. | |
| 5,599,291 A | 2/1997 | Balbierz et al. | |
| 5,676,688 A | 10/1997 | Jaker et al. | |
| 5,681,274 A | 10/1997 | Perkins et al. | |
| 5,711,841 A | 1/1998 | Jaker | |
| 5,814,058 A | 9/1998 | Carlson et al. | |
| 5,836,913 A | 11/1998 | Orth et al. | |
| 5,860,972 A | 1/1999 | Hoang | |
| 5,879,366 A | 3/1999 | Shaw et al. | |
| 5,897,535 A | 4/1999 | Feliziani et al. | |
| 5,972,019 A | 10/1999 | Engelson et al. | |
| 5,989,264 A | 11/1999 | Wright | |
| 6,007,488 A | 12/1999 | Jaker et al. | |
| 6,080,174 A | 6/2000 | Dubrul et al. | |
| 6,214,037 B1 | 4/2001 | Mitchell et al. | |
| 6,240,968 B1 | 6/2001 | Bigonzi-Jaker et al. | |
| 6,325,812 B1 | 12/2001 | Dubrul et al. | |
| 6,494,893 B2 | 12/2002 | Dubrul et al. | |
| 6,500,185 B1 | 12/2002 | Mathews et al. | |
| 6,623,508 B2 | 9/2003 | Shaw et al. | |
| 6,656,146 B1 | 12/2003 | Clayman et al. | |
| 6,692,484 B1 | 2/2004 | Karpiel et al. | |
| 6,709,465 B2 | 3/2004 | Mitchell et al. | |
| 6,929,664 B2 | 8/2005 | Kolb | |
| 6,945,950 B2 | 9/2005 | Clayman et al. | |
| 7,214,229 B2 | 5/2007 | Mitchell et al. | |
| 7,217,250 B2 | 5/2007 | Kolb | |
| 7,316,663 B2 | 1/2008 | Whitmore, III | |
| 7,462,183 B2 | 12/2008 | Behl et al. | |
| 7,674,283 B2 | 3/2010 | Mitchell et al. | |
| 7,682,366 B2 | 3/2010 | Sakurai et al. | |
| 7,698,205 B2 | 4/2010 | Romani | |
| 7,879,066 B2 | 2/2011 | Desai et al. | |
| 7,883,516 B2 | 2/2011 | Huang et al. | |
| 7,972,292 B2 | 7/2011 | Behl et al. | |
| 8,080,019 B2 | 12/2011 | Behl et al. | |
| 2001/0044595 A1 | 11/2001 | Reydel et al. | |
| 2002/0183853 A1 | 12/2002 | Mitchell et al. | |
| 2003/0040754 A1* | 2/2003 | Mitchell et al. | 606/106 |
| 2003/0050659 A1 | 3/2003 | Murphy et al. | |
| 2003/0078611 A1 | 4/2003 | Hashiba et al. | |
| 2003/0120281 A1 | 6/2003 | Bates et al. | |
| 2003/0153970 A1 | 8/2003 | Rao et al. | |
| 2003/0191492 A1 | 10/2003 | Gellman et al. | |
| 2003/0229332 A1 | 12/2003 | Intoccia | |
| 2004/0092956 A1 | 5/2004 | Liddicoat et al. | |
| 2004/0210239 A1 | 10/2004 | Nash et al. | |
| 2004/0220587 A1 | 11/2004 | Teague et al. | |
| 2004/0249470 A1 | 12/2004 | Whitmore, III | |
| 2005/0038447 A1 | 2/2005 | Huffmaster | |
| 2005/0060023 A1 | 3/2005 | Mitchell et al. | |
| 2005/0143678 A1 | 6/2005 | Schwarz et al. | |
| 2005/0197627 A1 | 9/2005 | Huang et al. | |
| 2005/0228481 A1 | 10/2005 | Manasas et al. | |
| 2006/0009784 A1 | 1/2006 | Behl et al. | |
| 2006/0116693 A1 | 6/2006 | Weisenburgh, II et al. | |
| 2007/0016244 A1 | 1/2007 | Behl et al. | |
| 2007/0088256 A1 | 4/2007 | Intoccia | |
| 2007/0191768 A1 | 8/2007 | Kolb | |
| 2008/0177277 A1 | 7/2008 | Huang et al. | |
| 2009/0287238 A1 | 11/2009 | Behl et al. | |
| 2011/0098690 A1 | 4/2011 | Huang et al. | |
| 2011/0172678 A1 | 7/2011 | Behl et al. | |

FOREIGN PATENT DOCUMENTS

| | | |
|---|---|---|
| JP | 2001-507598 | 6/2001 |
| WO | WO 99/23952 A1 | 5/1999 |
| WO | WO 2005/110244 A1 | 11/2005 |
| WO | WO 2006/014491 A2 | 2/2006 |
| WO | WO 2006/014491 A3 | 12/2007 |

OTHER PUBLICATIONS

European seach report and search opinion dated Jul. 7, 2010 for EP 05770447.0.

Garrido, et al. Utilizacion del cateter "stone sweeper" en la patologia litiasica del tracto urinario superior. [The use of Stone Sweeper catheter for stone disease of the upper urinary tract], Arch Esp Urol. Nov. 2006; 56(9):889-892. [English Abstract Only].

International search report and written opinion dated Aug. 15, 2008 for PCT/US2007/069182.

International search report and written opinion dated Nov. 5, 2007 for PCT/US2005/023988.

L'Esperance, et al. Ureteral Expanding Stent: A New Device for Urolithiasis. J Endourol. May 1, 2007; 21(5): 533-537.

Merriam-Webster definition of anchor as accessed on Jan. 31, 2013; http://www.merriam-webster.com/dictionary/anchor.

Merriam-Webster definition of surround as accessed on Jan. 31, 2013; http://www.merriam-webster.com/dictionary/surround.

Office action dated Feb. 7, 2011 for U.S. Appl. No. 12/269,739.
Office action dated Feb. 8, 2013 for U.S. Appl. No. 13/073,680.
Office action dated Apr. 14, 2008 for U.S. Appl. No. 10/886,886.
Office action dated May 25, 2010 for U.S. Appl. No. 11/777,515.
Office action dated Jul. 6, 2009 for U.S. Appl. No. 11/436,256.
Office action dated Jul. 22, 2010 for U.S. Appl. No. 11/436,256.
Office action dated Aug. 16, 2012 for U.S. Appl. No. 13/073,680.
Office action dated Sep. 15, 2010 for U.S. Appl. No. 12/269,739.
Office action dated Oct. 12, 2012 for U.S. Appl. No. 12/982,595.
Office action dated Oct. 13, 2009 for U.S. Appl. No. 11/436,256.
Office action dated Nov. 9, 2009 for U.S. Appl. No. 11/777,515.
Office action dated Dec. 10, 2008 for U.S. Appl. No. 11/436,256.

Woitzik, et al. Polyethylene sheath device to reduce tumor cell seeding along the needle tract in percutaneous biopsy. Surg. Endosc. 2003; 17:311-314.

Office action dated May 20, 2013 for U.S. Appl. No. 12/982,595.
Office action dated Oct. 3, 2013 for U.S. Appl. No. 12/982,595.
European search report and search opinion dated Dec. 11, 2013 for EP 077975589.7.

* cited by examiner

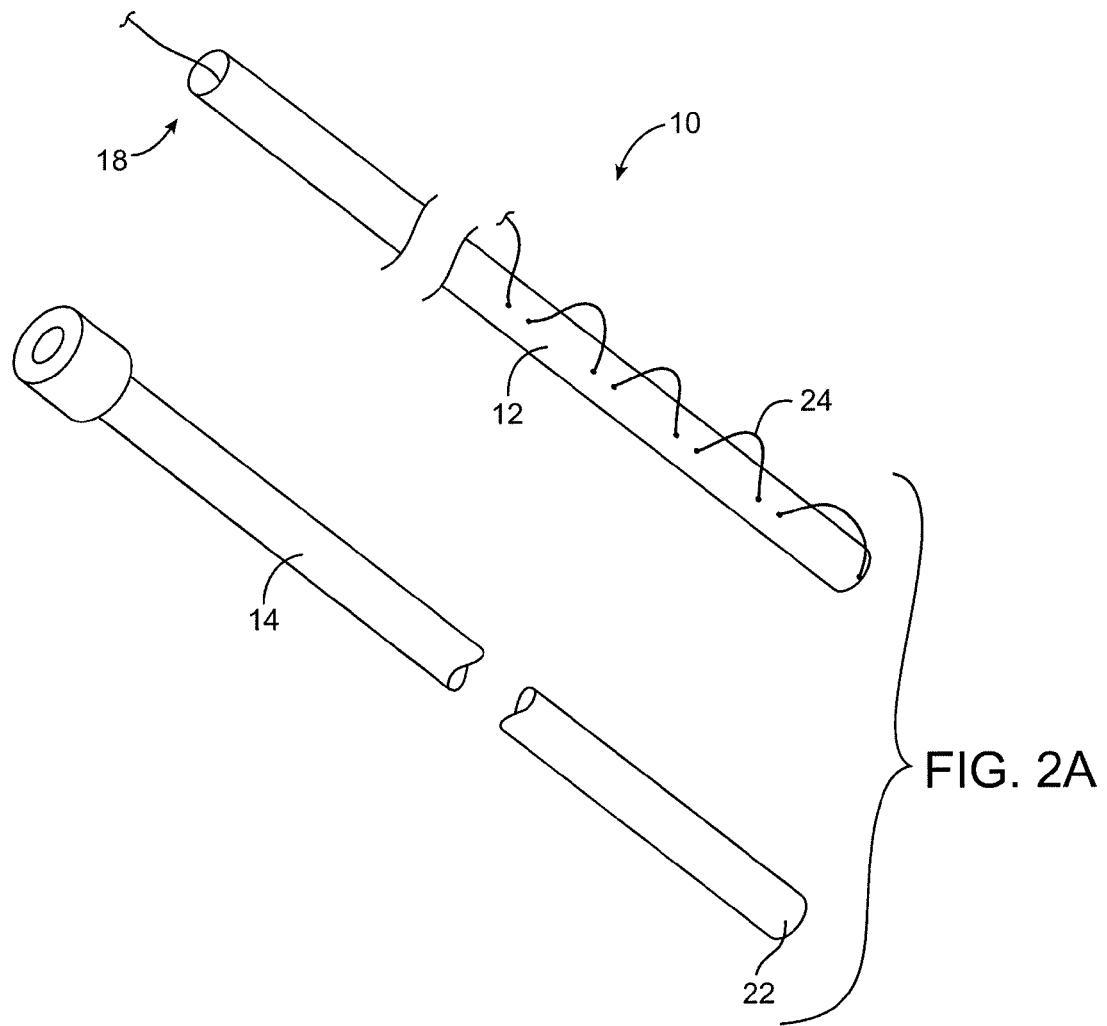
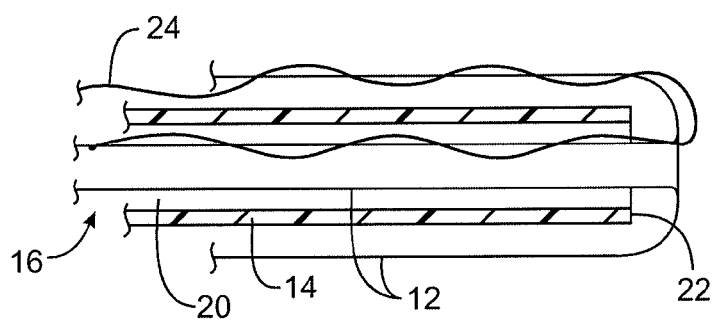
FIG. 2B

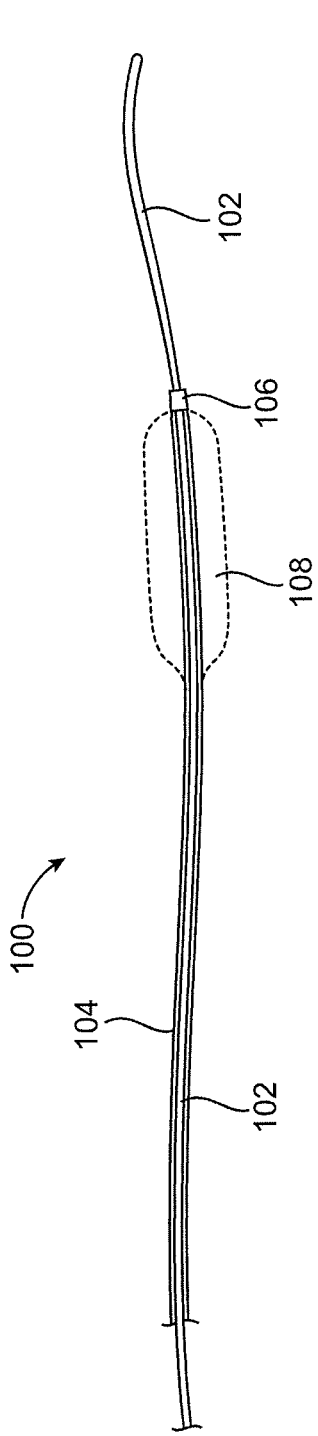
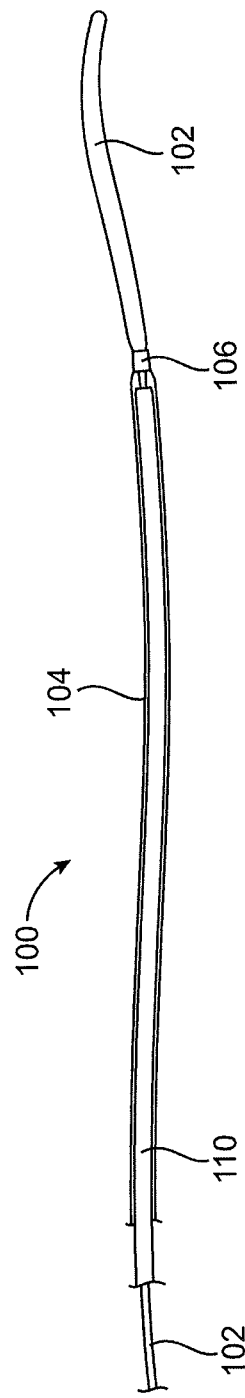

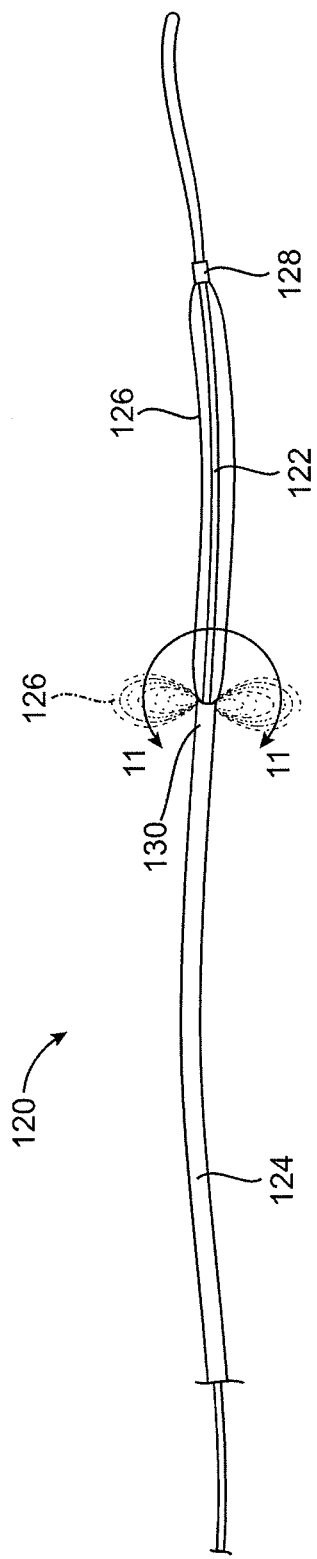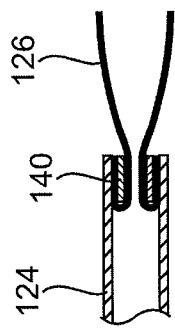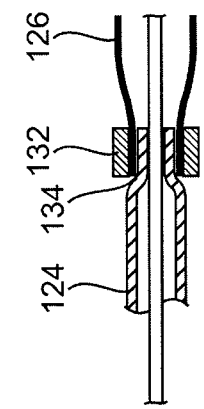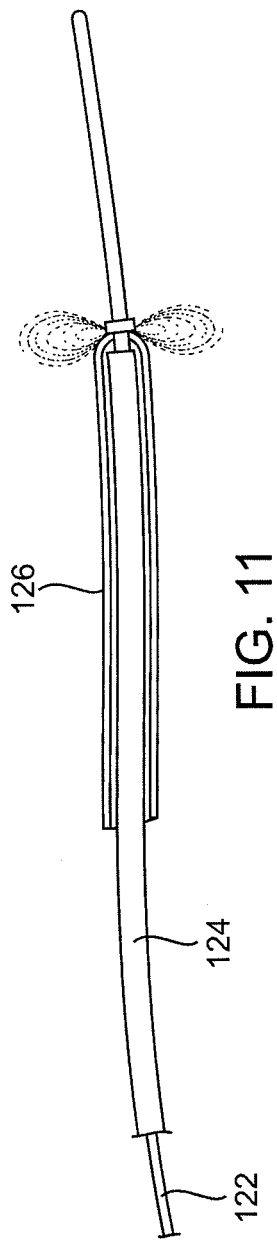

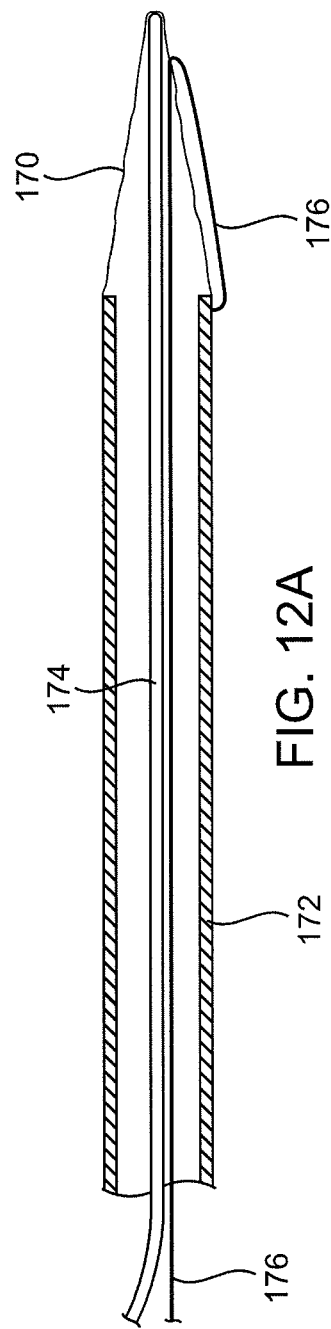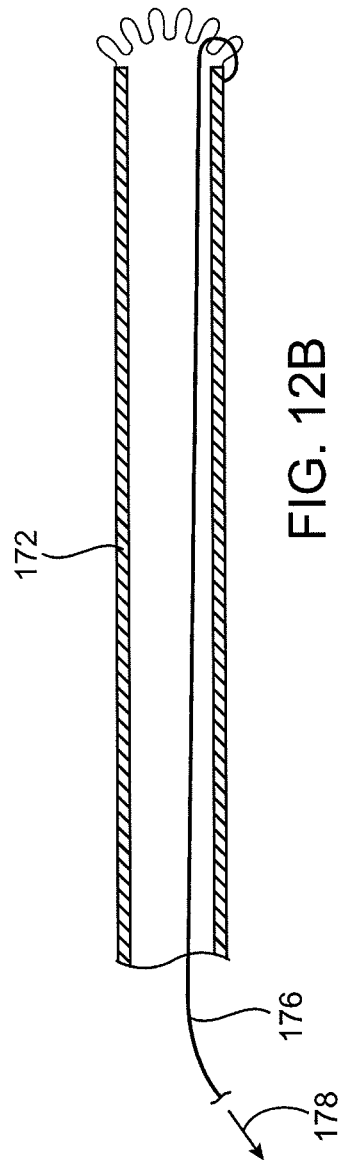
FIG. 12A
FIG. 12B

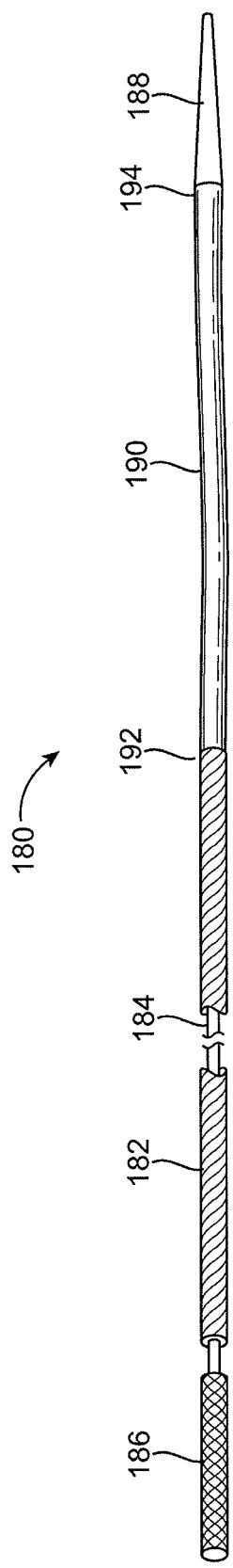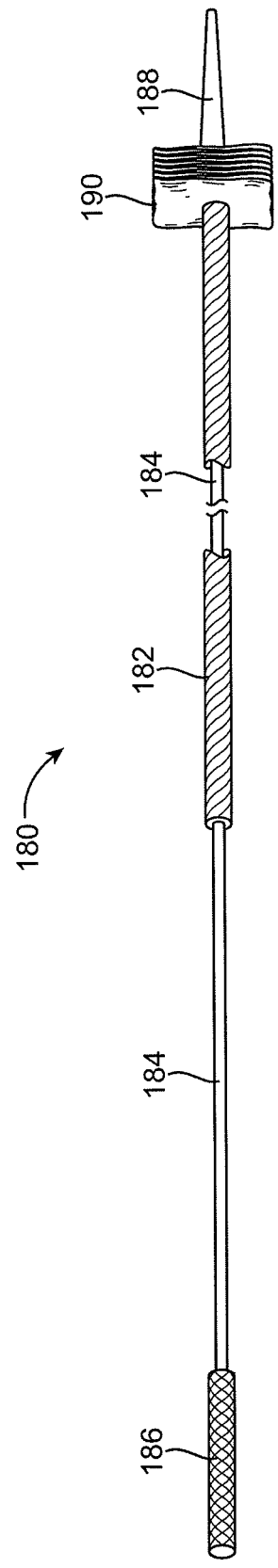

METHODS AND APPARATUS FOR DEPLOYING URETERAL STENTS

CROSS-REFERENCE TO RELATED APPLICATIONS

This application is a continuation of U.S. patent application Ser. No. 13/073,680, filed Mar. 28, 2011, which is a divisional of U.S. patent application Ser. No. 11/436,256, filed May 17, 2006, which is a continuation-in-part of PCT/US05/23988, filed on Jul. 6, 2005, which claimed the benefit of U.S. patent application Ser. No. 10/886,886, filed on Jul. 7, 2004, the full disclosures of which are incorporated herein by reference.

BACKGROUND OF THE INVENTION

1. Field of the Invention

The present invention relates generally to medical apparatus and methods. More particularly, the present invention relates to methods and apparatus for decompressing ureteral stones and blockages in other body lumens.

Calculi or "stones" can form in the kidneys as low solubility waste materials precipitate out of solution. The resulting "kidney stones" can pass into the ureter and, so long as the stones are relatively small, can pass from the patient through normal urination. Larger kidney stones which lodge in the ureter are referred to as ureteral stones can cause pain, particularly when they occlude the ureter and cause pressure to build in the kidneys.

Ureteral stones can be treated in a variety of ways. Most commonly, patients are given pain medication and fluids and the stones are allowed naturally pass from the ureter. In the remaining cases, where the pain is more severe or the build-up of pressure threatens to harm the kidney, the patient may be treated more aggressively to remove or destroy the stone. Common treatments include surgery, shock wave lithotripsy, laser lithotripsy, and the like.

Of particular interest to the present invention, stents may be placed from the kidney to the bladder to bypass the ureteral stone and allow drainage. Placement of such stents is often after prior treatment. Although it may be desirable to place a stent before treatment to decompress the kidney and relieve both pressure and pain, such prophylactic stent placement is rare. Stent placements are typically performed in an operating room where anesthesia and fluoroscopic imaging are available to aid and verify stent positioning. The need to use an operating room is a disadvantage of present procedure The risk of traumatizing and/or perforating the ureteral wall as a significant length of stent, is advanced past the stone in order to anchor one end in the kidney is another disadvantage of the present procedures. Furthermore, should the stone be dislodged and forced up the ureter, the procedure will be prolonged and the risk of trauma to the patient is increased.

For these reasons, it would be desirable to provide improved ureteral stent designs and methods for their placement. In particular, it would be desirable if the stents had a very low profile for placement, did not require anchoring within the kidney, and could be introduced without the need for full anesthesia and in settings other than an operating room. At least some of these advantages will be met by the inventions described hereinbelow.

2. Description of the Background Art

U.S. Pat. No. 6,709,465 and Published Application No. 2005/00600023 describe ureteral stents comprising a series of adjacent expanding structures for anchoring in the ureter. The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. A wire basket for advancing stone fragment through a body lumen during lithotripsy procedure is available under the Stone Cone tradename from Boston Scientific Corporation. See Published U.S. Application No. 2003/0120281. Copending application Ser. No. 10/794,337, filed on Mar. 5, 2004, the full disclosure of which is incorporated herein by reference, describes a sheath delivery system that could be used in performing some of the methods described herein.

SUMMARY OF THE INVENTION

The present invention provides methods and apparatus for decompressing ureteral stones, more commonly known as kidney stones, which block a patient's ureter. By "decompressing," it is meant that a small leakage path will be created and maintained which bypasses the ureteral stone and allows urine to drain from the kidney to the bladder. While the volumetric rate of drainage may be small, the ability to drain the kidney at even a very low rate is of great benefit to the patient since it reduces pain and the risk of damage to the kidneys. The devices of the present invention will be easy to place, will be less traumatic than present day techniques for placing ureteral stents, and will reduce or eliminate the need for full anesthesia and/or use of an operating room. In some cases, the present invention will facilitate passing of the ureteral stone into the bladder, providing significant pain relief and obviating the need for continued pain medication. In other cases, the decompression methods of the present invention will be useful to reduce pain while the patient waits for lithotripsy or other conventional ureteral stone therapeutic methods.

In a first aspect of the present invention, a method for decompressing a ureteral stone comprises advancing a small guide member through a ureter past the ureteral stone. An anchor on the guide member is then deployed distal to the stone, serving to hold the guide member in place. The deployed anchor will be adapted so that it will not fully occlude the ureter, even though it has been compressed and expanded across at least a portion of the ureter, so that the anchor allows the leakage of urine and the guide member creates a further leakage path past the stone. Usually, the anchor will be deployed immediately distal to the stone, but in other instances it may be deployed at a spaced-apart distance distally of the stone.

The guide member used in the methods of the present invention may take a variety of forms. Typically, it will be a guidewire, usually having a straight, floppy or a steerable tip and dimensions which are generally used for ureteral guidewires. Alternatively, the guide member could comprise a hollow tube, coil or other member, and said hollow guide members could be advanced through an everting sheath in a manner described in detail below. When using an everting sheath for introduction, the anchor can comprise at least a portion of the everting sheath, where that portion has been advanced past the ureteral stone. In other instances, the hollow member may itself be advanced over a previously introduced guidewire.

Deploying the anchor may be performed in a variety of ways. Most commonly, the anchor will be deployed by longitudinally shortening a compressible structure carried by a guide member. Often, longitudinally shortening the compressible structure will comprise simply drawing the guide member proximally in the ureter so that the compressible structure engages the ureteral stone and compresses or compacts against the stone, where the compacted structure serves to anchor the guide member while being adapted to permit leakage of urine through the structure. In some instances, the anchor may apply an expulsion force on the stone, for example as a result of normal peristalsis, where the expulsion force may over time dislodge the stone into the bladder.

Alternatively, longitudinal shortening of the compressible structure may comprise drawing a tether, filament, shaft, guidewire, core, or other tension member attached to the distal end of the compressible structure to pull and compress the structure together. Usually, the proximal end of the compressible structure will be carried by a separate tubular carrier, where the tubular carrier and tension member are adapted to slide relative to each other to compress and lengthen the compressible member. Exemplary compressible structures include strips, sleeves, ribbons, tubes, and the like. For example, the compressible structure may comprise a tubular, compactable sleeve carried over the guidewire.

In a second aspect of the present invention, a device for decompressing a ureteral stone in a ureter of a patient comprises a guide member and an anchor. The guide member may be advanced from a ureteral os in a bladder past the ureteral stone in the ureter. The anchor is disposed near a distal end of the guide member and is adapted to compress in situ immediately distal to the stone. Thus, the anchor may be expanded in a non-occluding form to anchor the guide member and create a leakage path past the stone.

The guide member may take a variety of forms, typically being an elongate member capable of being advanced through the urethra and bladder and into the ureter. The guide member may comprise a wire or a tube, and the anchor will typically comprise a length of material carried on the wire or tube. The length of material may comprise a strip, sleeve, ribbon, tube, or the like. The material is typically selected from the group consisting of polymer films, woven fabrics, non-woven fabrics, and composites and laminates thereof. The length of material may be modified in a variety of ways to enhance or promote leakage of urine therethrough. For example, the material may be perforated or porous, it may be formed from a loosely woven material having a variety of leakage paths therethrough, may include surface features, fold lines, deformations, or the like, which prevent full compression of the material and leave a variety of flow paths through the material even when fully compressed. In exemplary embodiments, the length of material may have a "C" or "H" shaped pattern when compressed to provide the desired bypass flow paths. It will be appreciated that the fully compressed anchor structure need only allow a relatively low flow rate of urine. Urine flow from a kidney in an adult male is typically on the order of 1 to 1.5 ml/minute. The device will usually allow a flow of at least 0.5 ml/minute, more usually at 1 ml/minute, and preferably greater than 2 ml/minute, in order to achieve adequate decompression (pressure reduction) in the kidneys.

As a presently preferred aspect of the present invention, a device for decompressing a ureteral stone in a ureter of a patient comprises a guidewire and a compressible anchor attached to the guidewire. The guidewire will comprise a proximal shaft and a distal steerable or straight tip. The anchor is attached at or near the junction between the distal tip and the proximal section of the guidewire. The anchor is folded, stretched, or otherwise packed in a low profile configuration on the guidewire during advancement of the guidewire through the ureter and past the stone. The anchor is arranged and adapted so that it can be deployed to expand radially outwardly to anchor within the ureter to hold the guidewire in place. The anchor may be deployed by drawing it proximally against a ureteral stone in the ureter. Alternatively, the device may include a deployment mechanism to pull back or otherwise expand the anchor in the ureter. Typically, the guidewire will have length in the range from about 100 cm to 200 cm, preferably from 120 cm to 160 cm.

The guidewire will usually comprise a distal portion and a removable proximal portion. The distal portion will have a length in the range from about 20 cm to 40 cm, and the separable proximal portion will have a length in the range from about 80 cm to 160 cm. In this way, after the distal section of the guidewire has been properly positioned in the ureter, and the anchor deployed, the proximal portion may be detached from the distal portion, leaving the distal portion in place, preferably with a pre-formed pigtail or other anchoring structure in the distal portion remaining in the bladder.

The device may further comprise a retrieval cord attached to the proximal end of the distal length of the guidewire to facilitate retrieval of the device from the patient.

As with prior embodiments, the anchor may comprise a tube, strip, sleeve, ribbon, or the like. The anchor will typically be relatively short so that it may be advanced entirely beyond the stone to facilitate pull back and compression of the anchor. Typically, the anchor will have a length before deployment in the range from about 2 cm to 8 cm, usually from 3 cm to 45 cm, while still on the guidewire. An anchor may comprise any of the materials suggested above for the anchors, including polymer films, woven fabrics, non-woven fabrics, and composites and laminates thereof. The anchor material may also be slit, porous or perforated or otherwise modified to promote leakage of urine therethrough when compressed. Likewise, the anchor may be designed in a non-occluding "compressed" configuration, such as a "C" or "H" shape, wherein a flow channel remains open, after compression occurs.

BRIEF DESCRIPTION OF THE DRAWINGS

FIGS. 2A and 2B illustrate a first apparatus in accordance with the present invention which comprises a sleeve-like length of material, a tubular guide, and a tension member.

FIG. 7 illustrates apparatus according to the present invention having a guidewire-like advancement member.

FIG. 8 illustrates an embodiment of the present invention similar to that shown in FIG. 7, but further including a stiffening tube which may be slidingly advanced over a proximal portion of the guidewire.

FIG. 9 illustrates an embodiment of the present invention comprising a guidewire-like advancement member, a tubular sheath, and a tubular length of material connected between the advancement member and tubular sheath.

FIGS. 10A and 10B illustrate alternative detailed constructions taken along line 10-10 of FIG. 9.

FIG. 11 illustrates one possible manner in which the length of material of the apparatus of FIG. 9 may be stowed.

FIGS. 12, 12A-12D illustrate further embodiments of the apparatus of the present invention where the length of material may be tensioned directly from its proximal end.

DETAILED DESCRIPTION OF THE INVENTION

The methods and apparatus of the present invention are useful for decompressing ureteral or kidney stones in the ureter of a patient. The ureteral stones can, in some cases, fully occlude the ureter and cause a build-up of pressure within the kidney since fluids can no longer pass through the ureter. The decompression devices and methods of the present invention are useful for placing a tube, wire, or similar structure past the stone and anchoring that structure in place to promote leakage of urine past the stone and relieve pressure within the kidney.

Figure 1:
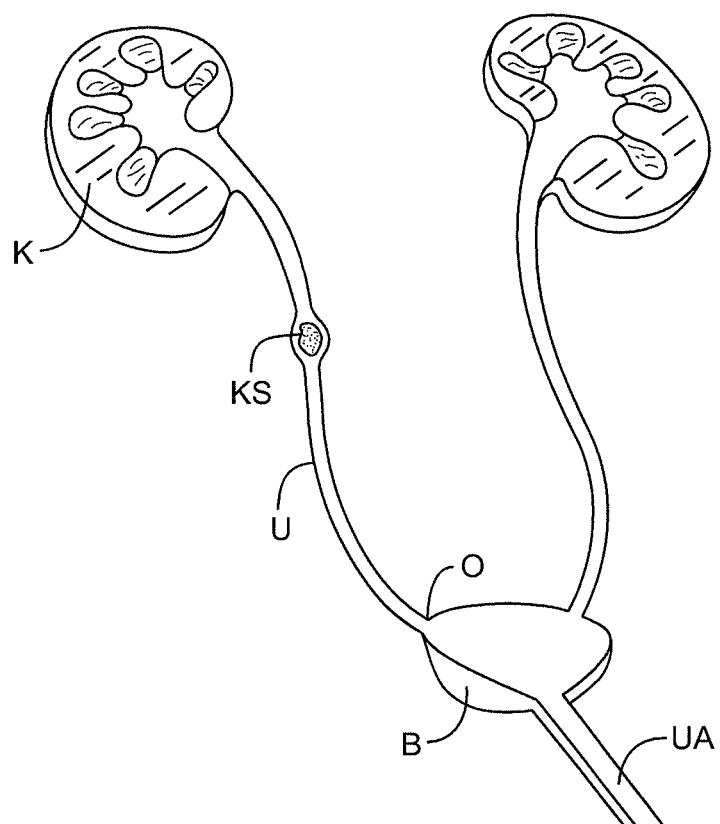
FIG. 1 illustrates a ureter having a kidney stone lodged between the kidney and bladder.

Referring now to FIG. 1, the present invention may be used for decompressing a ureteral or kidney stone KS or fragments from a ureter U between a kidney K and a bladder B. Access to the bladder will be through the urethra UA using conventional access devices which will not be described herein. Access to the ureter U will be through the os O in a wall of the bladder leading into the lumen of the ureter.

A first exemplary system 10 for performing the methods of the present invention comprises a sleeve-like length of material 12 and a tubular guide 14, as shown in FIGS. 2A and 2B. The sleeve-like length of material 12 has a trailing end 16 and an anchor end 18. The length of the sleeve-like length of material will typically be in the range from 1 cm to 10 cm, usually from 2 cm to 6 cm, although much longer lengths may find use in different circumstances. The sleeve may have a continuous sidewall with no openings (other than at the trailing end 16 and anchor end 18), but will preferably have open regions, have a loose weave in the case of woven materials, or otherwise have openings, discontinuities, or surface features in the sidewall so that when it is compressed in the ureter, it will be non-occluding. By "non-occluding," it is meant that urine from the kidney will be able to pass through the compressed structure and bypass the ureteral stone, as described in more detail below.

Referring now in particular to FIG. 2B, the sleeve-like length of material 12 may be arranged so that it is initially within a central passage 20 of the tubular guide 14. The material 12 can be arranged so that the anchor end 18 of the sleeve-like length of material 12 will initially be on the exterior of the tubular guide 14 and generally held stationary as the tubular guide is advanced. As the tubular guide 14 is advanced through the body lumen, the trailing end 16 is everted over the distal end 22 of the guide member, generally as shown in FIG. 2B. The trailing end 16 will usually include a tension member 24 which may be a suture, filament, thin wire, or other element which is attached at or near the terminus of the trailing end 16 and which preferably is woven in and out of the material 12 over at least a portion of the length of material 12. Such woven or pleated structures will be described in more detail hereinbelow. Pulling on the tension member 24 will collapse and compact the length of material 12 in order to provide the desired luminal anchor.

Referring now to FIGS. 3A-3G, use of the system 10 for decompressing a ureteral or kidney stone KS in a lumen L of a ureter U will be described. Initially, access is gained to the os O of the bladder B (FIG. 1) in a conventional manner. The tubular guide 14 will then be passed through the os O and into the lumen L of the ureter with the anchor end 18 of the sleeve-like member 12 being held stationary relative to the os. Specific systems for doing this are described in copending application Ser. No. 10/794,337, the full disclosure of which is incorporated herein by reference.

Figure 3A:
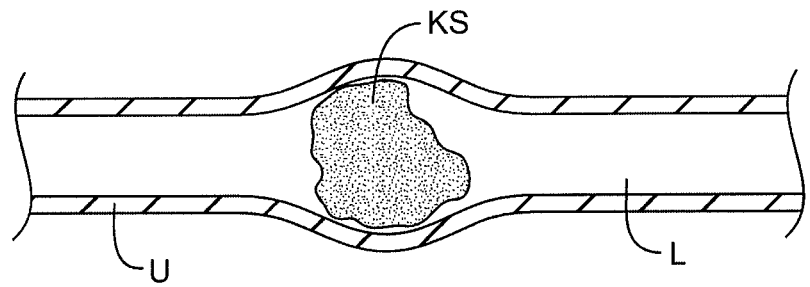
FIGS. 3A-3G illustrate use of the apparatus of FIGS. 2A and 2B for removing a kidney stone from a ureter.
Figure 3B:
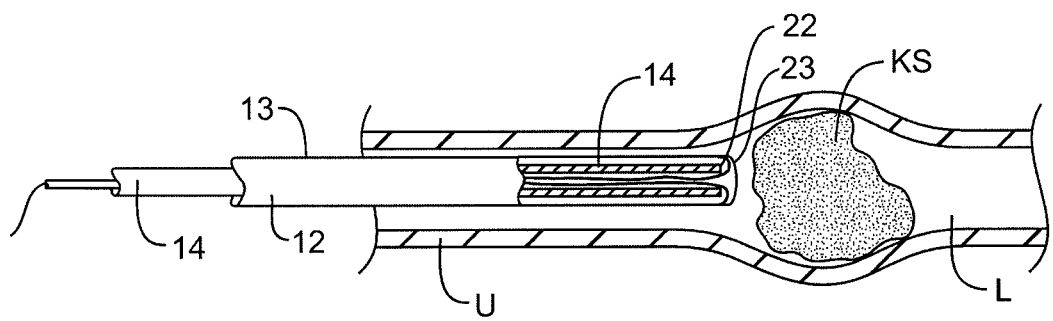
Figure 3C:
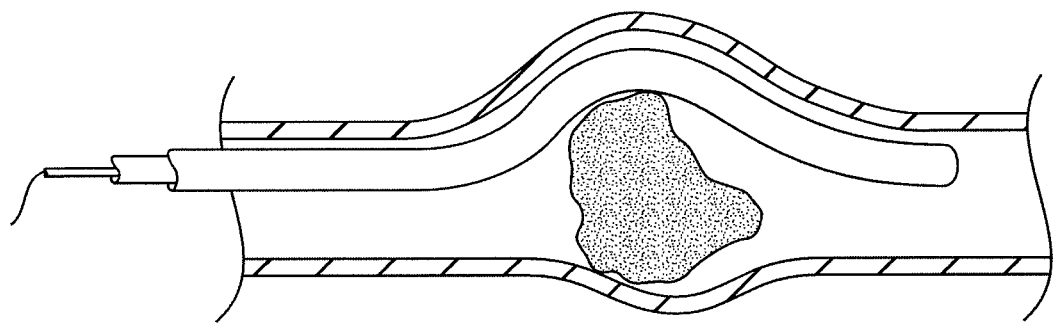

Referring now to FIG. 3B, the tubular guide 14 is advanced so that the sleeve-like length of material 12 everts from the distal end 22 of the guide. As the everting end 23 of the tubular guide 14 approaches the kidney stone KS, the sleeve-like length of material 12 will continue to be everted, but will have an exposed surface 13 which remains generally stationary relative to the inner wall of the ureter U and the exterior of the kidney stone KS. Such eversion of the sleeve-like length of material 12 acts like a "tractor tread" in allowing the tubular guide 12 to bypass the kidney stone, as illustrated in FIG. 3C. In addition to facilitating bypass of the kidney stone KS, the eversion of the length of material 12 also reduces the risk of perforation or other trauma to the ureter.

Figure 3D:
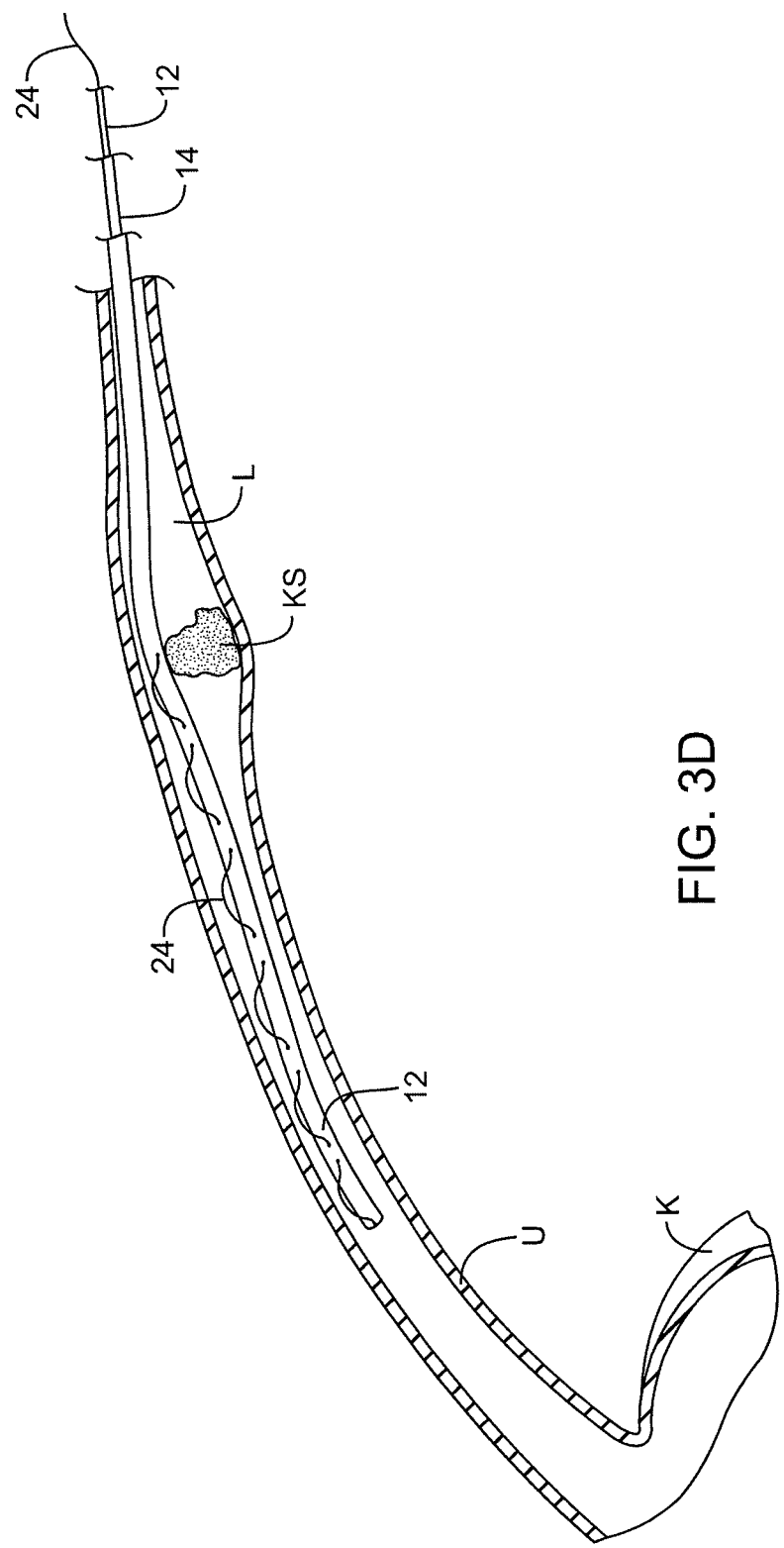

Referring now to FIG. 3D, once past the kidney stone KS, the tubular guide 14 will continue to be advanced through the lumen L in the distal direction (toward the kidney K) until the trailing end 16 has been partly or fully exposed so that the region including the tension member 24 lies distal to the kidney stone KS.

Figure 3E:
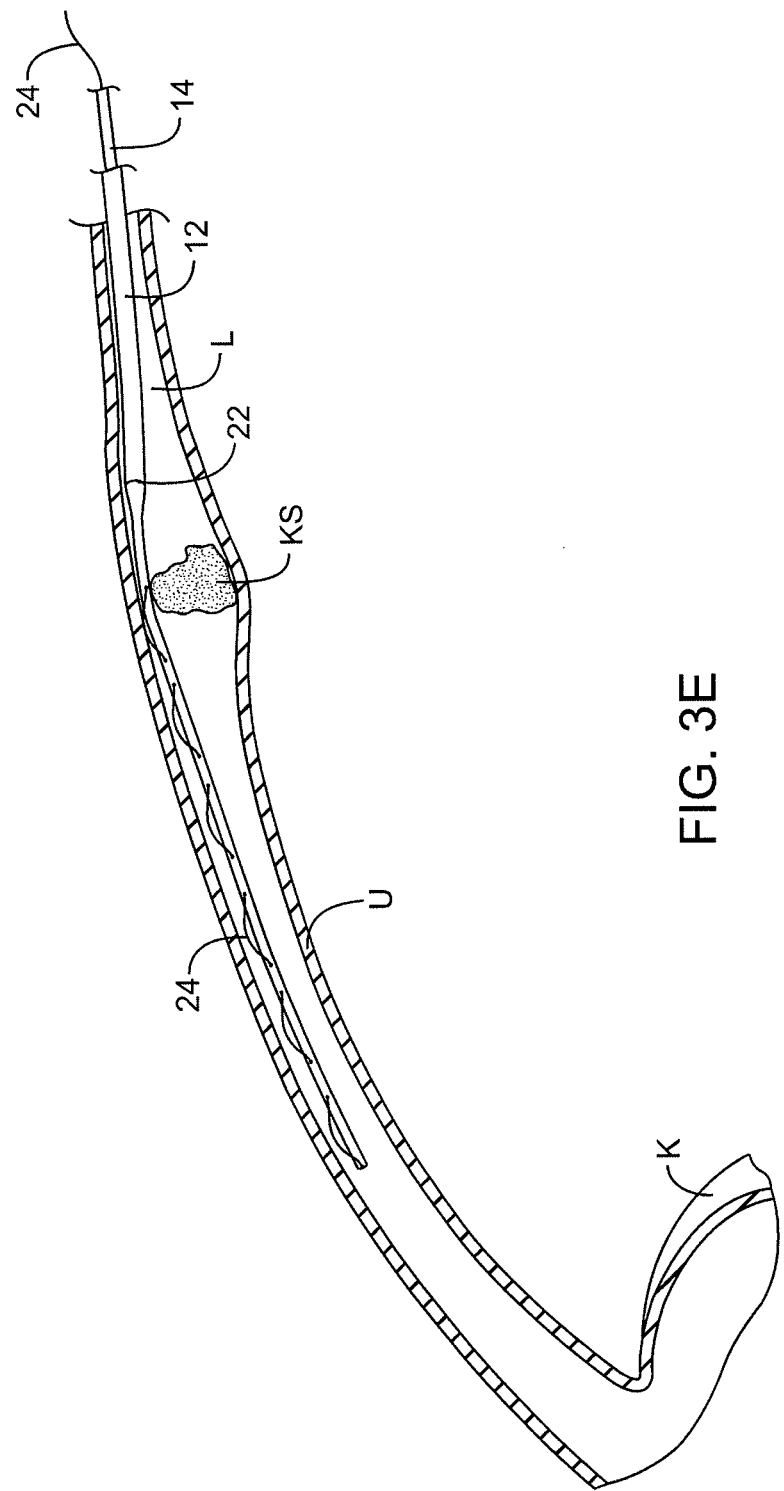
Figure 3F:
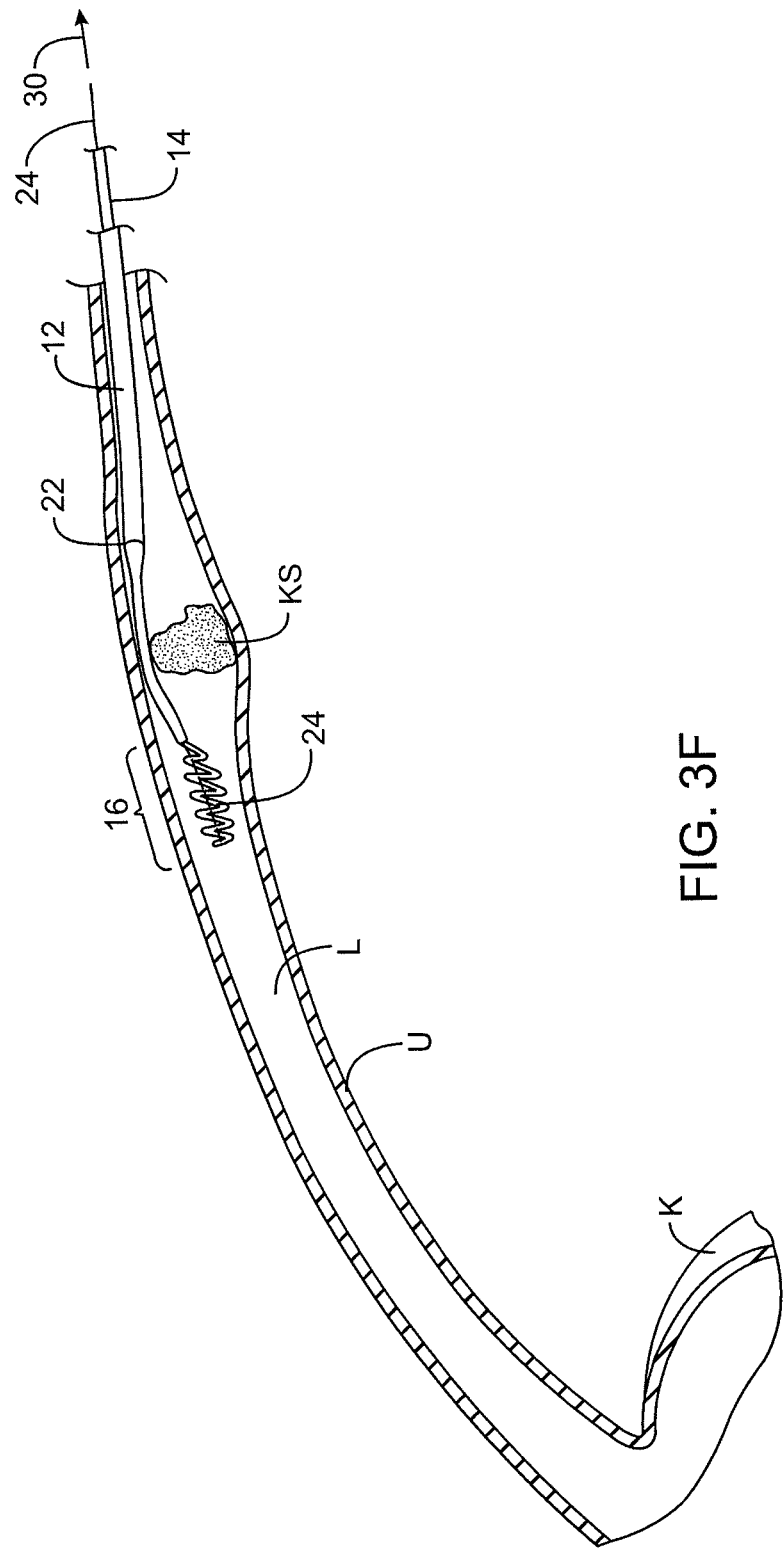

At this point, the tubular guide 14 will be at least partly withdrawn in a proximal direction so that its distal end 22 is located proximal of the kidney stone KS, as shown in FIG. 3E. The portion of the sleeve-like member 12 which lies distal to the kidney stone will radially collapse (since its internal support has been withdrawn) leaving a slack "shell" having the tension member 24 laced therethrough in place. By drawing in a proximal direction (arrow 30) on tension member 24, the trailing end 16 of the sleeve-like member 12 will be caused to axially collapse, generally in the manner of an accordion, as shown in FIG. 3F. By continuing to draw on the tension member 24 the trailing end 16 of the sleeve-like member 12 will be compacted against a distal surface of the kidney stone KS, as shown in FIG. 3G.

Figure 3G:
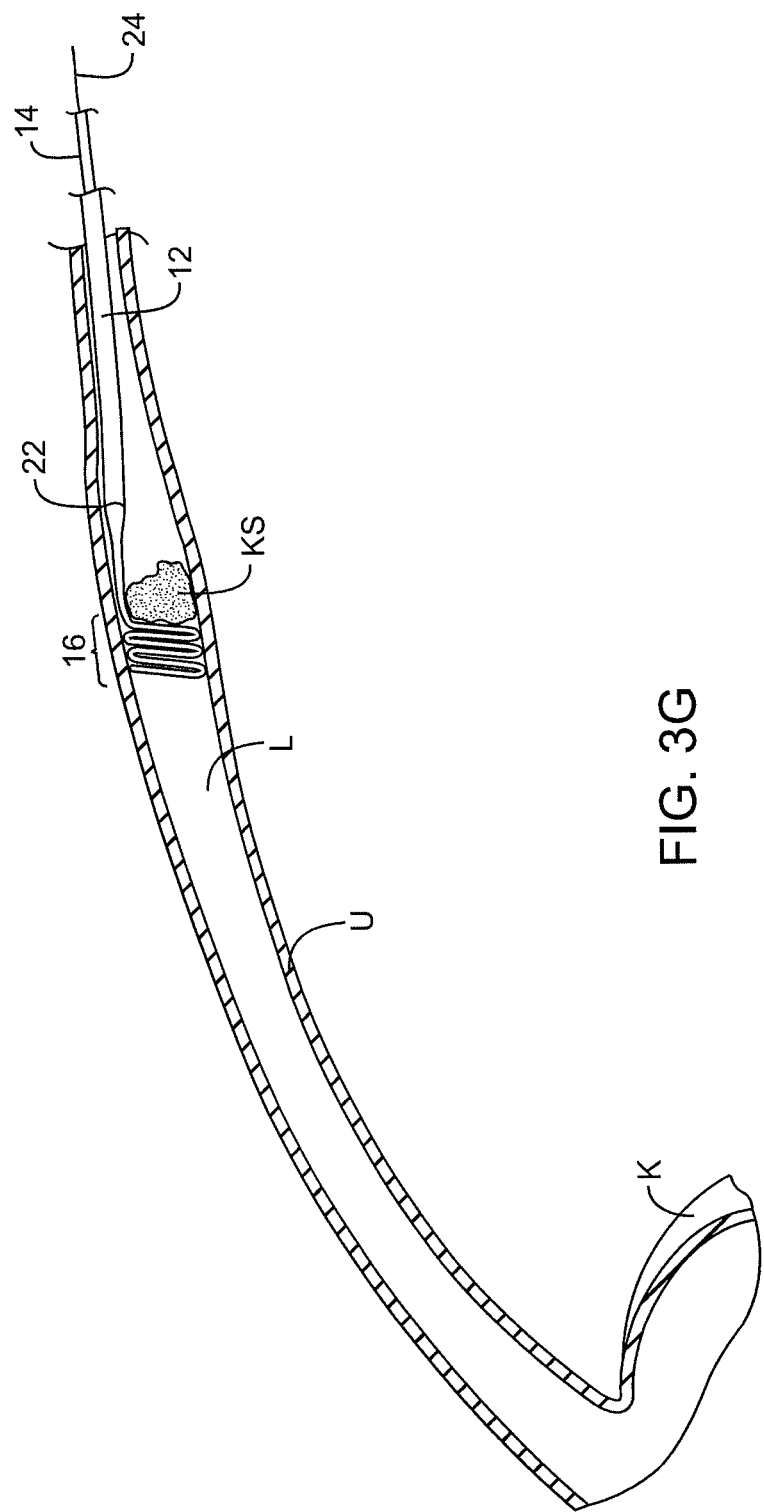

The compacted trailing edge 16 of the sleeve-like member 12 will serve to anchor the remaining portion of the sleeve and optionally the tubular guide (unless the tubular guide is removed) within the ureter as shown in FIG. 3G. The material or other structural characteristics of the sleeve-like member 12 will be selected so that the compact region 16 does not occlude the lumen L of the ureter U, but instead provides a flow or leakage path to the stone while the portion of the sleeve which passes by the side of the kidney stone KS will similarly be constructed so that it provides the desired leakage path past the stone to permit decompression of the kidney K.

Figure 4A:
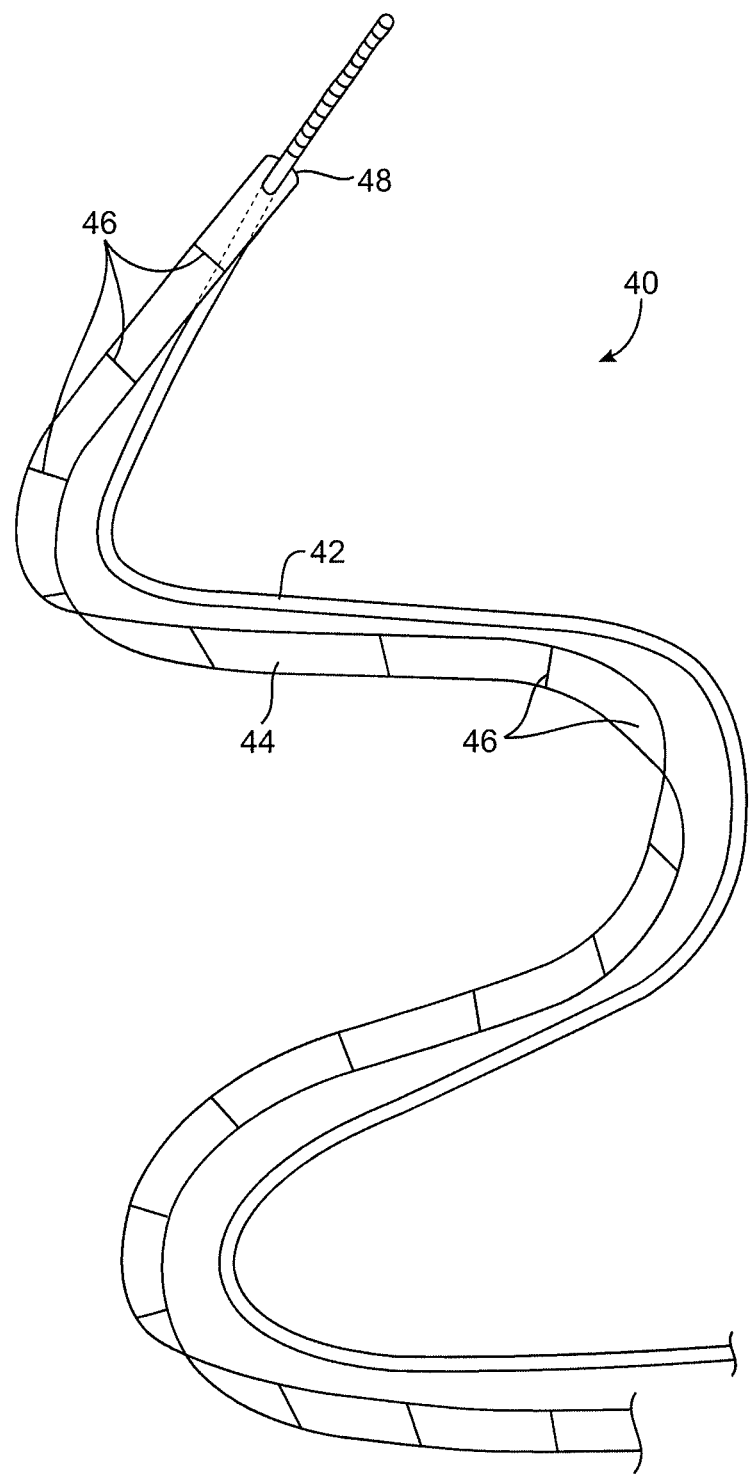
FIG. 4A illustrates a second apparatus constructed in accordance with the principles of the present invention consisting of a length of material and a separate advancement member.
Figure 4B:
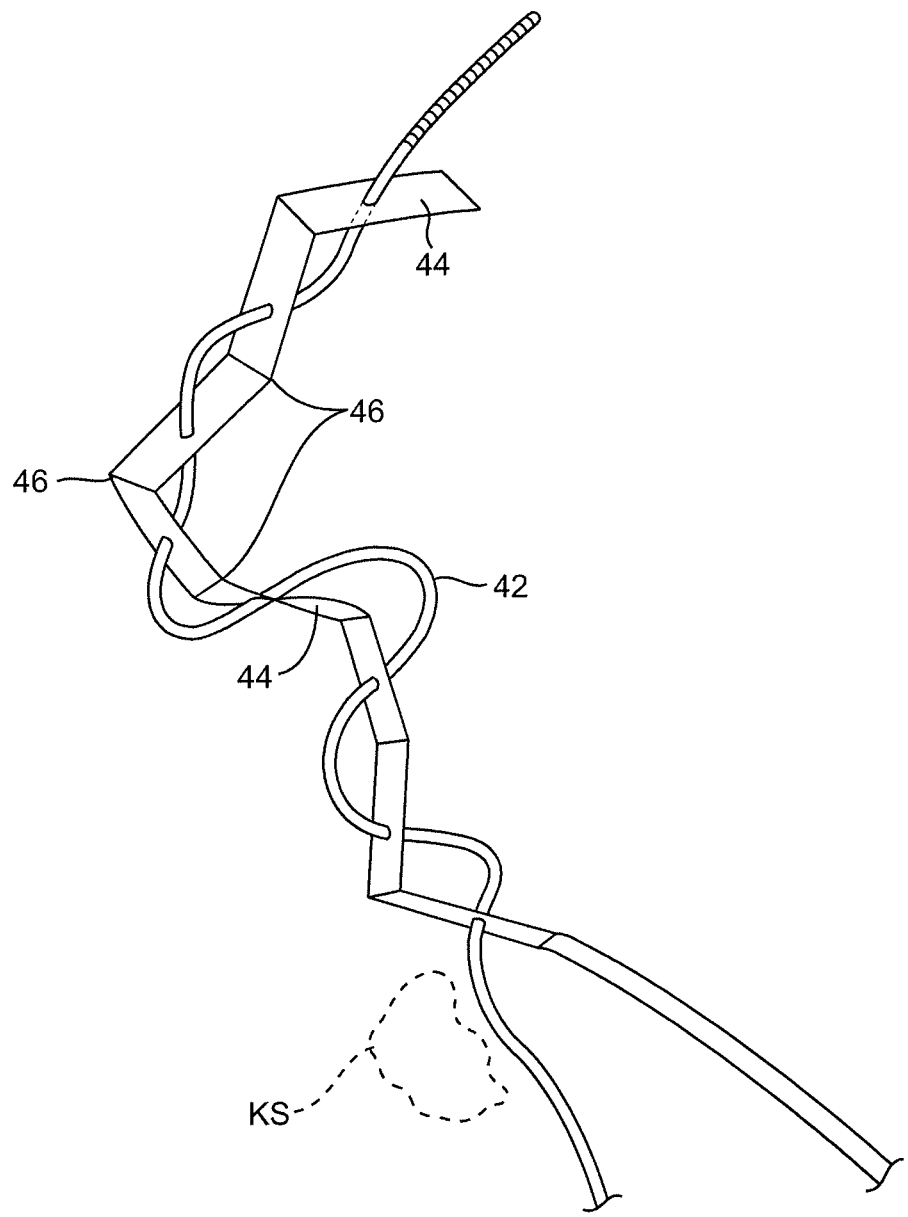
FIG. 4B illustrates a third apparatus similar to the second apparatus of FIG. 4A, except that the advancement member is threaded through a portion of the ribbon-like length of material.

Referring now to FIG. 4A, an alternative construction of the apparatus of the present invention will be described. System 40 comprises an advancement member 42 and a ribbon-like length of material 44. The advancement member may be a solid-core wire, a tube, or other small diameter or flat/thin member having sufficient column strength to permit its advancement through body lumen and preferably past a kidney stone in a ureter. For example, the advancement member may be in the form of a guidewire of the type commonly used in urological procedures. The ribbon-like length of material 44 may be composed of any of the materials listed previously and may have a length in the ranges set forth above. The length of material 44 will typically consist of only a single layer with a width in the range from 1 mm to 10 mm, usually from 2 mm to 6 mm, and a thickness of 1 mm or less. Optionally, the ribbon-like length of material 44 will comprise a flattened tube or other multiple-layer or laminated structure instead of a single layer as illustrated. The ribbon-like length of material 44 may also have a plurality of axially spaced-apart fold structures 46 disposed over at least a distal length thereof. A distal end 48 of the length of material 44 will be attached at or near a distal end of the advancement member 42 so that the advancement member can pull or otherwise carry the ribbon-like length of material through the target body lumen as it is advanced. Optionally, as shown in FIG. 4B, the advancement member 42 can be penetrated or "laced" through axially spaced-apart locations on the ribbon-like length of material 44. As illustrated, the lacing occurs through consecutive sections defined by the fold structures 46. In both cases, the advancement member 42 will be used to advance at least a portion of the ribbon 44 past a stone KS or other object to be retrieved or stabilized.

Figure 5A:
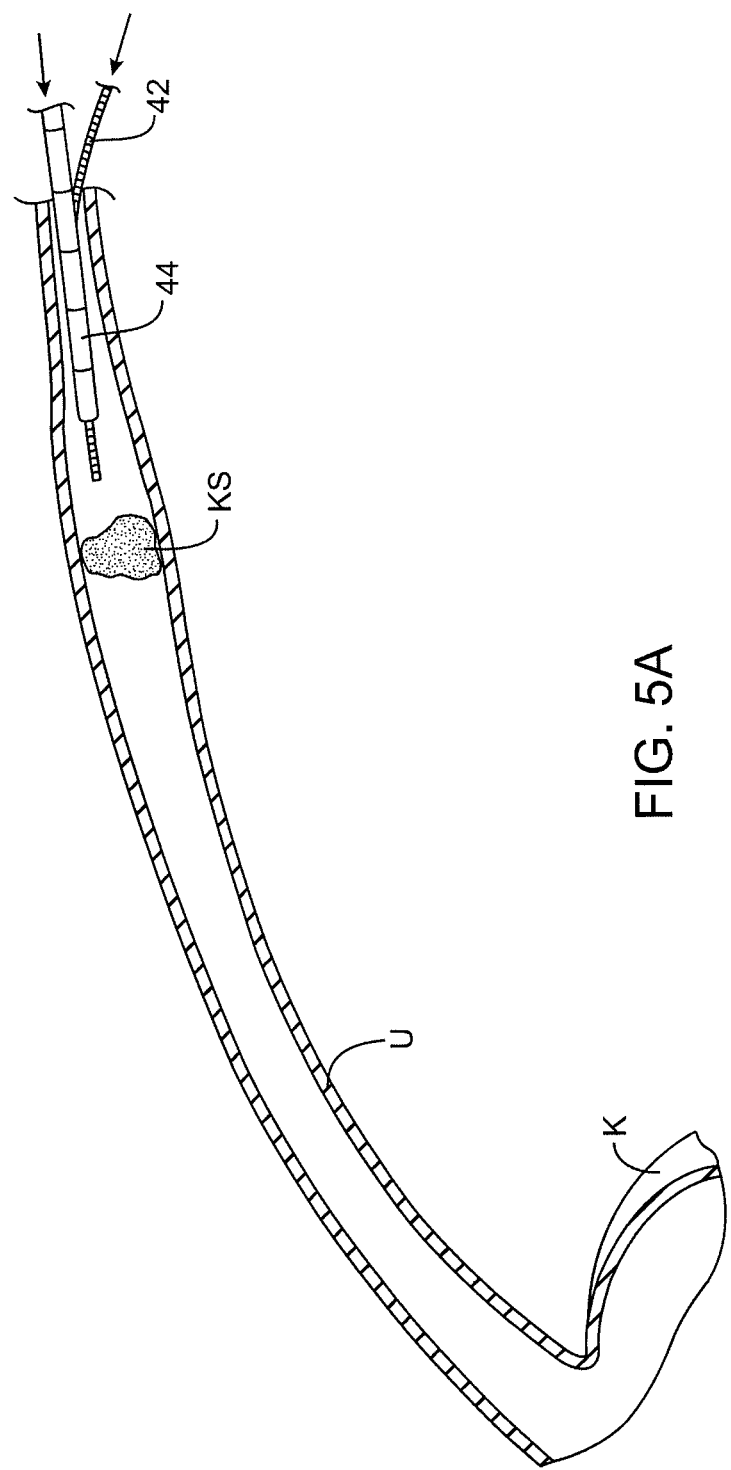
FIGS. 5A-5C illustrate use of the apparatus of FIG. 4A in accordance with the principles of the present invention.
Figure 5B:
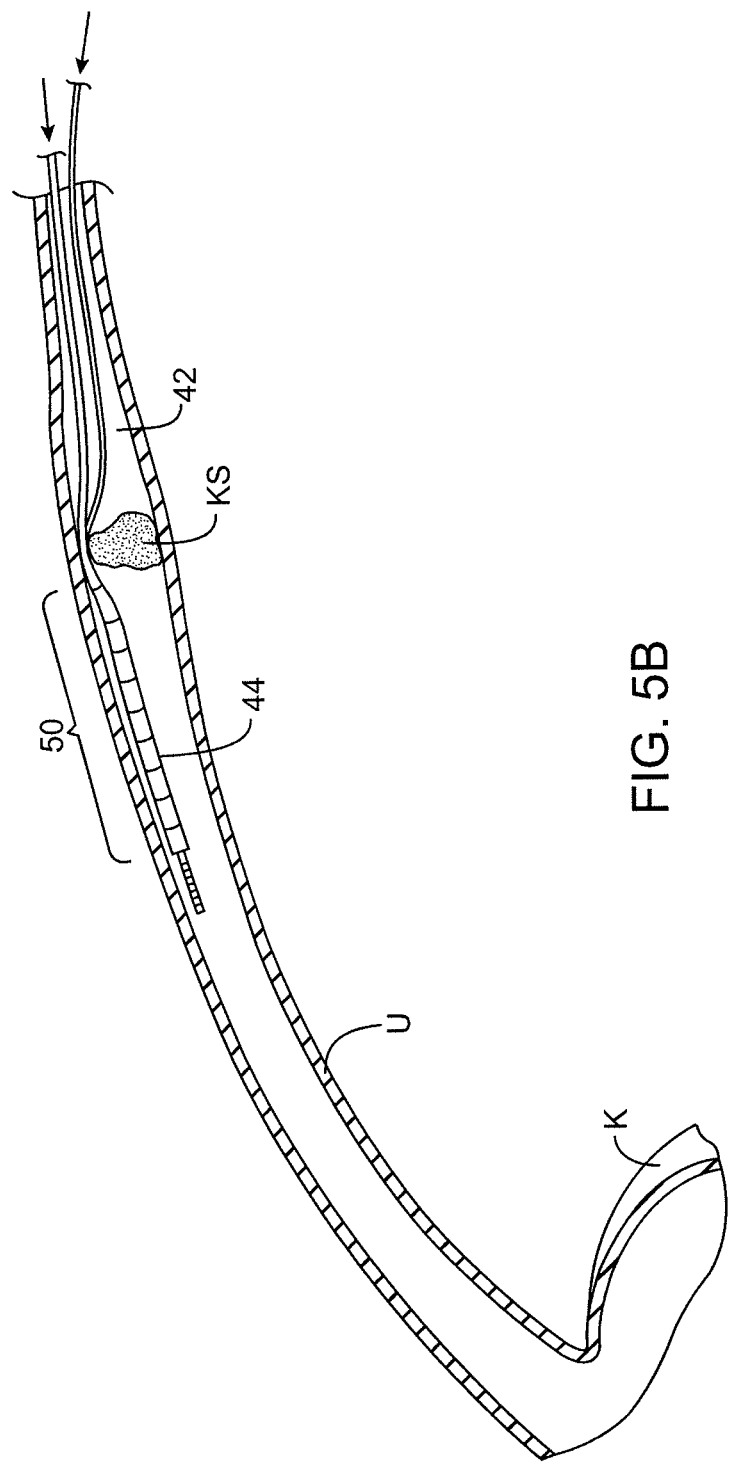
Figure 5C:
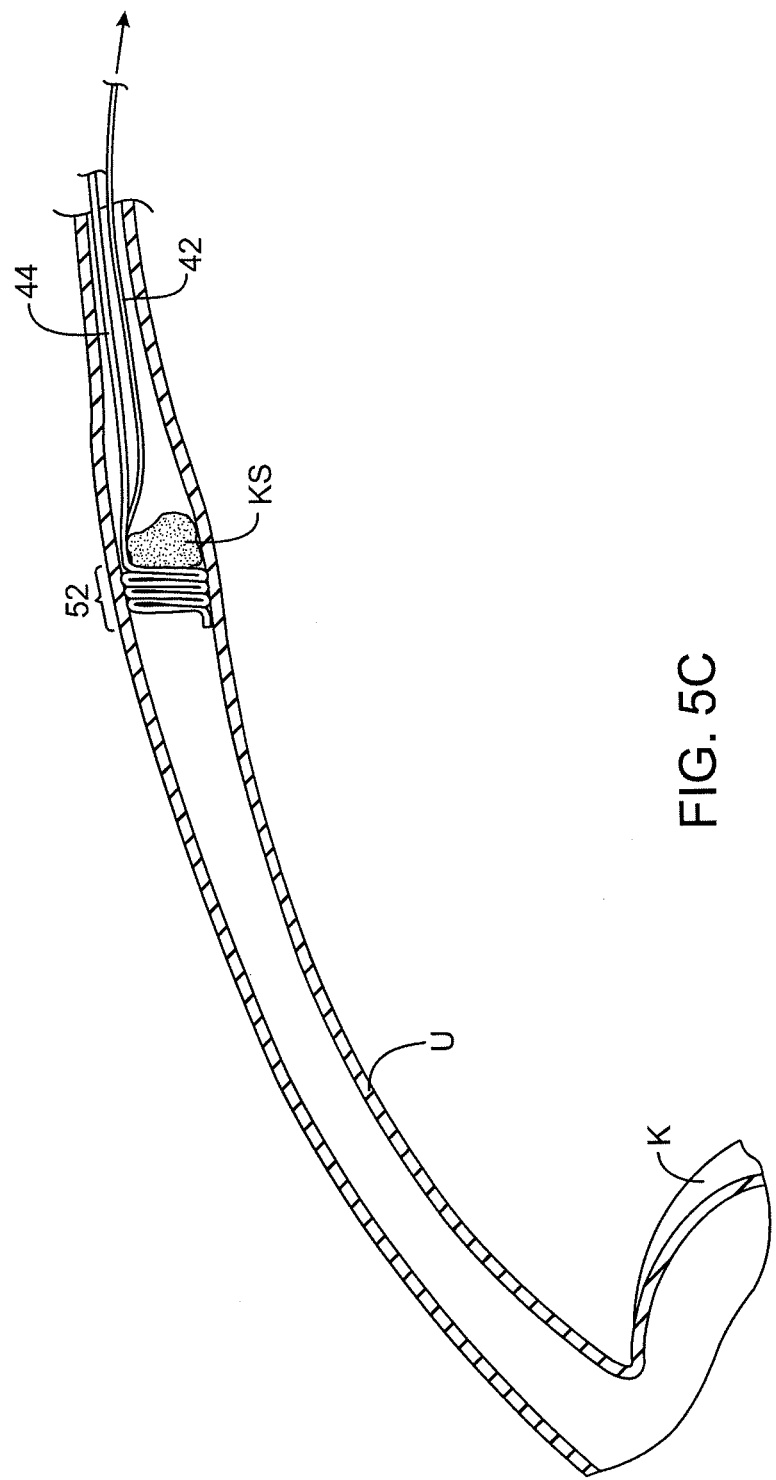

In use, the deployment system 40 of FIG. 4A is introduced by advancing advancement member 42 through the os O (FIG. 1) and into the lumen of the ureter U, as shown in FIG. 5A. The advancement member 42 carries the ribbon-like length of material 44 distally within the lumen and past the kidney stone KS as shown in FIG. 5B. After the desired distal positioning has been achieved, the advancement member 42 may be drawn in the proximal direction, as shown in FIG. 5C, while the proximal portion of the ribbon-like length of material 44 is left in place. In this way, a region 50 of the ribbon-like length of material 44 which is distal to the kidney stone KS, as shown in FIG. 5B, may be simultaneously or sequentially compacted into the foreshortened anchoring structure 52, as shown in FIG. 5C.

Figure 4C:
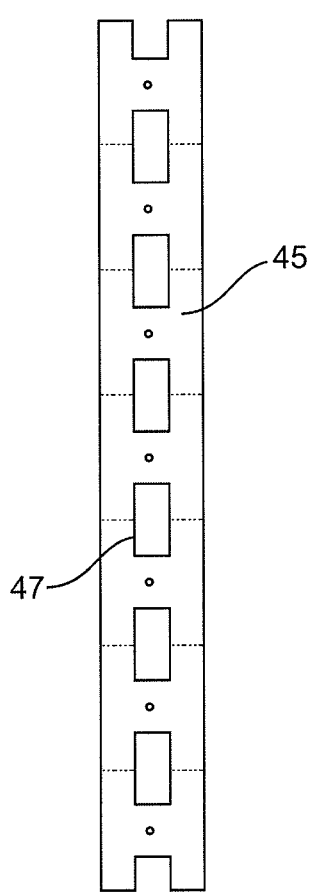
FIGS. 4C-4F illustrate alternate non-occluding configurations of the compressible length of material.
Figure 4E:
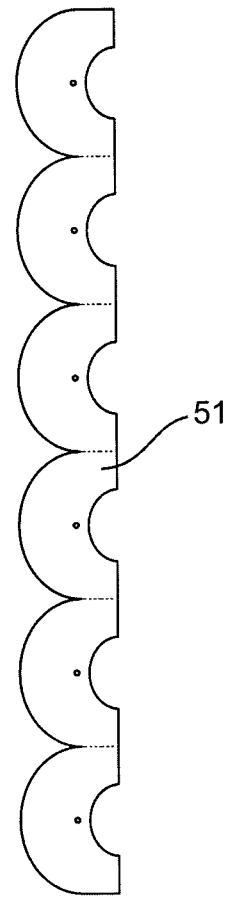
Figure 4D:
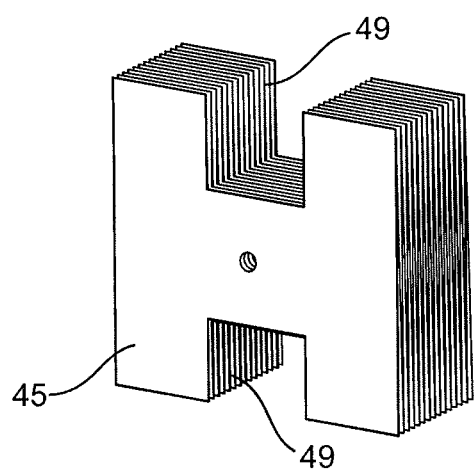
Figure 4F:
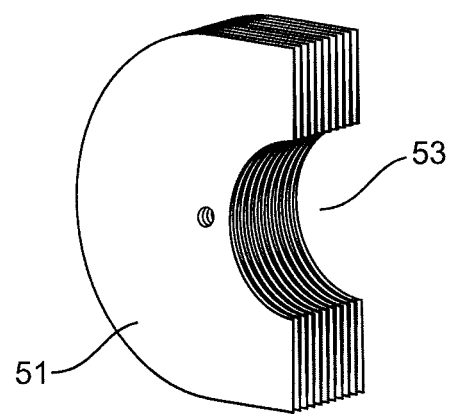

The anchors of the present invention may also be configured as elongate strips having particular patterns which, when folded or otherwise compressed, provide bypass channels to help assure that the deployed anchors will not occlude the ureter to prevent or inhibit urine flow. For example, as shown if FIGS. 4C and 4D, a ribbon-like length of material 45 may have cut-outs 47 which define bypass flow channels 49 when the material is folded, as shown in FIG. 4D. Alternatively, a length of material 51, as shown in FIG. 4E may have a C-shaped profile which, when folded, as shown in FIG. 4F, provides a C-shaped bypass flow channel. It will be appreciated, of course, that a wide variety of other configurations could be provided to assure that bypass flow channels are left after the anchor is folded or otherwise compacted within the ureter.

Figure 4G:
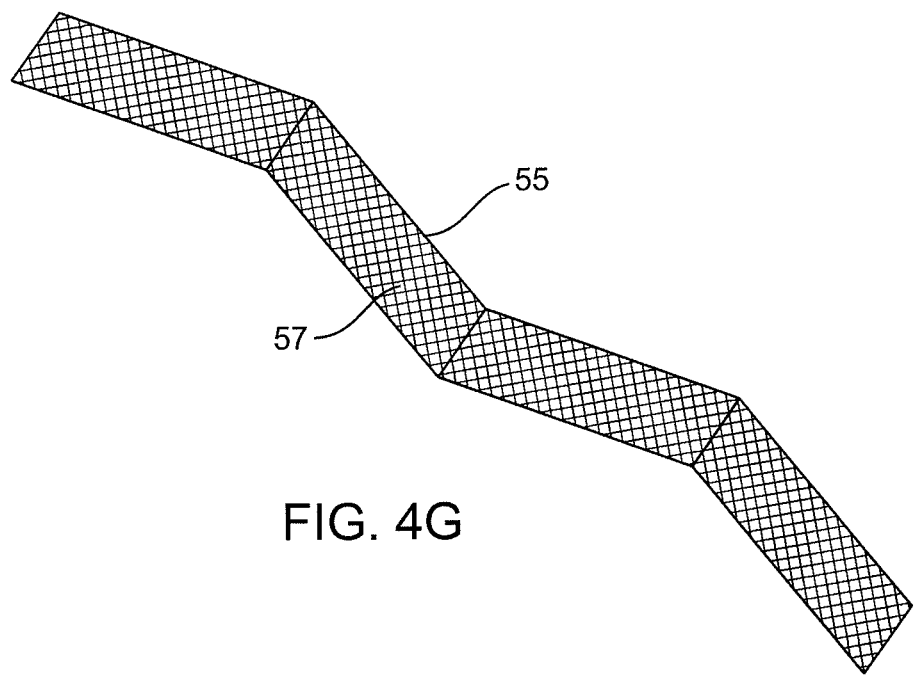
FIGS. 4G and 4H illustrate ribbon anchors having radiopaque layers thereon.
Figure 4H:
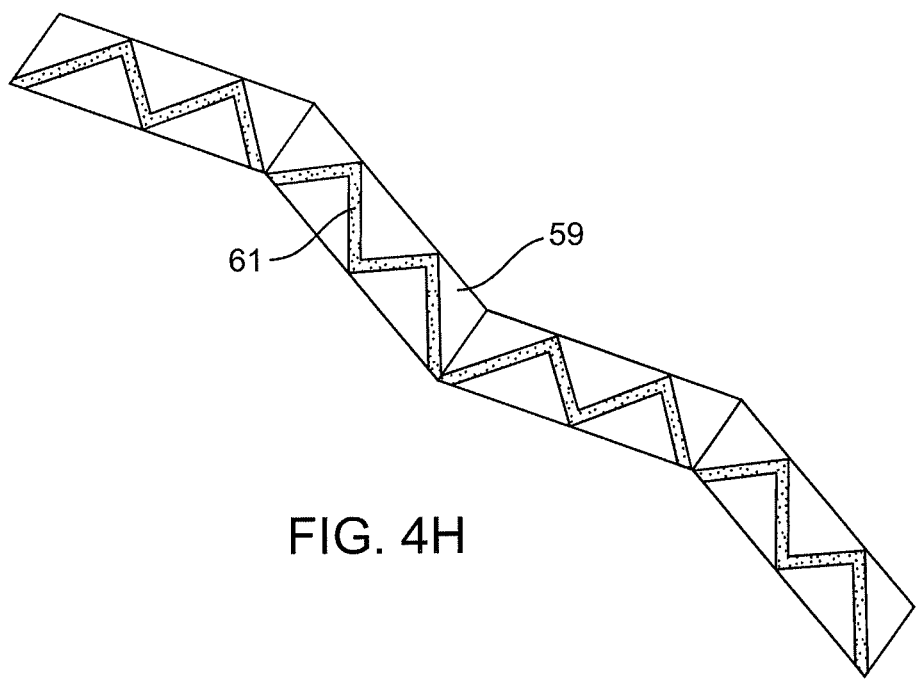

Referring now to FIGS. 4G and 4H, it will often be desirable to coat, imprint, laminate, or otherwise provide a layer or pattern of radiopaque material on at least one surface of the anchor. As shown in FIG. 4G, a length of material 55 is laminated to a layer of gold foil 57 over substantially its entire surface. It will be appreciated that when the length of material 55 folds into its compacted configuration, the gold foil will be layered to greatly enhance the radiopacity of the anchor structure. As shown in FIG. 4H, a similar length of material 59 has a radiopaque ink pattern 61 formed over a surface thereof. The pattern is shown as a zig-zag pattern, but a variety of other patterns could also be suitable. The radiopaque ink could also be formed generally uniformly over the entire surface, or both surfaces, of the length of the material 61. Again, when the length of material is folded or otherwise compacted, the radiopacity of the resulting anchor structure will be greatly enhanced as the layers of radiopaque ink are superimposed upon one another.

The foreshortened anchoring structure 52, as with previously described anchoring structures, will be perforated, porous, or otherwise structurally modified to assure that a leakage path exists through the compacted structure. In the embodiment illustrated in FIG. 5C, the leakage path past the kidney stone KS may be provided by either the advancement member 42, the length of material 44, or a combination of both.

Figure 6A:
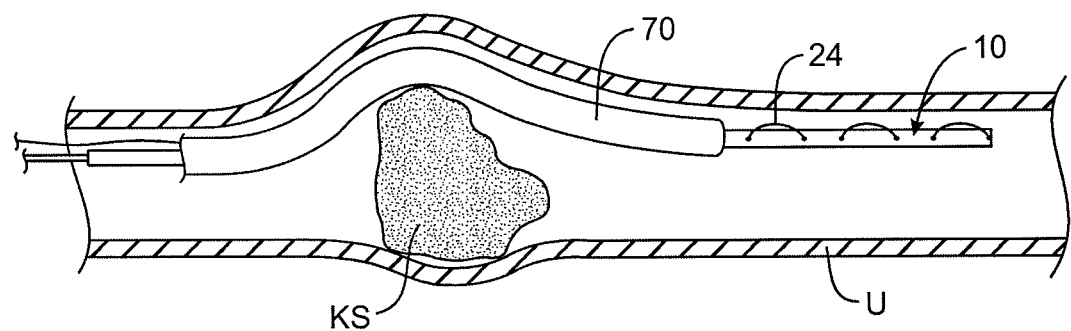
FIGS. 6A and 6B illustrate a modified protocol according to the principles of the present invention.
Figure 6B:
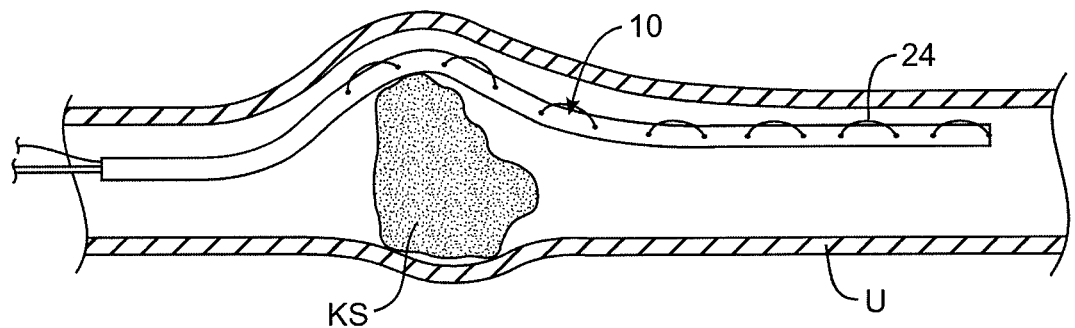

As described thus far, the material compaction systems 10 and 40 have been shown to be directly introduced, i.e. introduced without an external sheath or other introducing member. As shown in FIGS. 6A and 6B, however, any of the material compaction systems may be introduced through a sheath 70 which is first introduced into the lumen of the ureter U in a conventional manner. The sheath 70 may be a simple tubular sheath or could be an everting-sleeve sheath of the type described in copending application Ser. No. 10/794,337, the full disclosure of which has previously been incorporated herein by reference. In any event, once the sheath 70 is in place past the kidney stone KS, the sheath may be withdrawn leaving the material compaction system in place. System 10 is illustrated, but system 40 or any other systems according to the present invention could be introduced through the sheath. Once the system 10 is in place, it may be foreshortened by drawing on tension member 24 using the resulting compacted component as an anchor for the decompression structure in any of the ways described previously.

In certain embodiments of the present invention, a guidewire-element can be used as the advancement member. As shown in FIG. 7, an apparatus 100 comprises a guidewire 102 having a tubular length of material 104 attached at its distal end 106. Optionally, a distal region 108 (shown in broken line) of the tubular length of material 104 may be expanded, slit, braided, or otherwise modified so that it assumes a larger structure or mass when axially compacted in accordance with the principles of the present invention.

Referring now to FIG. 8, the apparatus of FIG. 7 may be modified to include a stiffening tube 110 which may be slid over the proximal end of the guidewire 102. This stiffening tube is advantageous in that it can improve pushability of the guidewire to advance past difficult obstructions in a body lumen. Once the guidewire is past the ureteral stone, the stiffening tube can be partially or wholly withdrawn, leaving the smaller guidewire 102 in place.

Referring now to FIG. 9, a further exemplary embodiment of an apparatus 120 of the present invention comprises a guidewire-like advancement member 122, a tubular guide member 124, and a tubular length of material 126. The tubular length of material 126 is attached at its distal end 128 to the guidewire and at its proximal end 130 to the tubular guide member 124. The attachment may be as shown in FIG. 10A where a ring 132 clamps the tubular length of material 126 over necked down region 134 of the tubular guide member 124. Alternatively, a clamping ring 140 may be provided within the distal end of the lumen of the tubular guide member 124, as shown in FIG. 10B. Although illustrated as a simple tube, the material 126 could further comprise an axial strip heat-sealed or otherwise attached over and coextensive with all or part of the tube so that the tube provides an axial lumen to receive the guidewire, while the axial strip provides additional mass or bulk when the structure is collapsed.

In the apparatus 120, the tubular length of material 126 may be elongated by advancing the advancement member 122 distally relatively to the tubular guide member 124. Alternatively, the length of material 126 may be compacted into its expanded mass, as shown in broken line in FIG. 9, by drawing the advancement member proximally relative to the tubular guide member 124. For introduction, the tubular guide 126 may be either elongated, as shown in FIG. 9, withdrawn into the lumen of the tubular guide member 124, or folded back over the exterior lumen of the guide member 124, as shown in FIG. 11.

Figure 12:
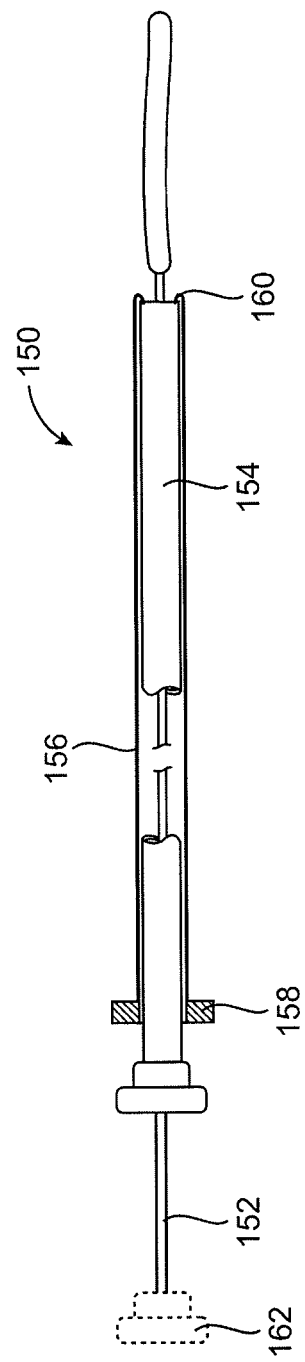

Referring now to FIG. 12, still another embodiment 150 of the apparatus of the present invention is illustrated. The apparatus 150 comprises a guidewire-like advancement member 152, a tubular guide 154, and a distal end 160 of the length of materials attached to the distal end of the guide tube. In this way, the guide tube can be advanced over the separate guidewire 152 (having a removable hub 162). The length of material 156 can then be enlarged into an anchoring mass by pulling proximally on the guide tube 154. Alternatively, the anchoring mass may be straightened and elongated by pulling proximally on the ring 158.

FIGS. 12A and 12B illustrate a closed-end collapsible structure 170 pushed in place by a wire 172 within a central lumen of a tube 174. A control tether 176 which may be a suture or other filament or flexible cord runs through the lumen of tube 172 to the distal end of collapsible structure 170 where the tether penetrates through the structure to the outside and loops back to where it is attached to the tube, preferably near the distal end of the tube as illustrated. When in place, the wire 174 is removed from the tube 172, and the tether 176 is tensioned proximally (arrow 178) to cause the structure to collapse, as shown in FIG. 12B, to form a bulbous mass of greater width than the width of the structure would otherwise allow in a strictly axial compression. The resulting shape may be similar to that of a "toilet brush". The collapsible structure may be formed from any of the materials described above for the ribbon structures of the present invention.

Referring now to FIGS. 12C and 12D, yet another embodiment of the apparatus of the present invention is illustrated. Apparatus 180 is a guidewire structure having an outer coil 182 and an inner core wire 184. The inner core wire 184 has an actuator grip 186 at its proximal end and is attached to a flexible tip 188, typically formed from polyurethane or other soft polymer, at its distal end. A generally tubular film structure 190 is attached at its proximal end 192 to the shaft 182 and at its distal end 194 to the flexible tip 188. Thus, by pulling proximally on the grip 186, the flexible tip 188 will be pulled toward the shaft 182, thus compressing the tubular structure 190, as shown in FIG. 12D. The tubular structure 190 can be formed in a variety of ways and could be continuous or discontinuous. It could further be formed as a braid or other foramenous structure, or even as a plurality of axial elements. In all cases, the tubular structure 190 will be radially expanded as it is axially compressed. In the illustrated embodiment, a flat sheet is heat-sealed around the core wire so that the expanded structure looks like a series of layered rectangular pieces, as illustrated.

Figure 13:
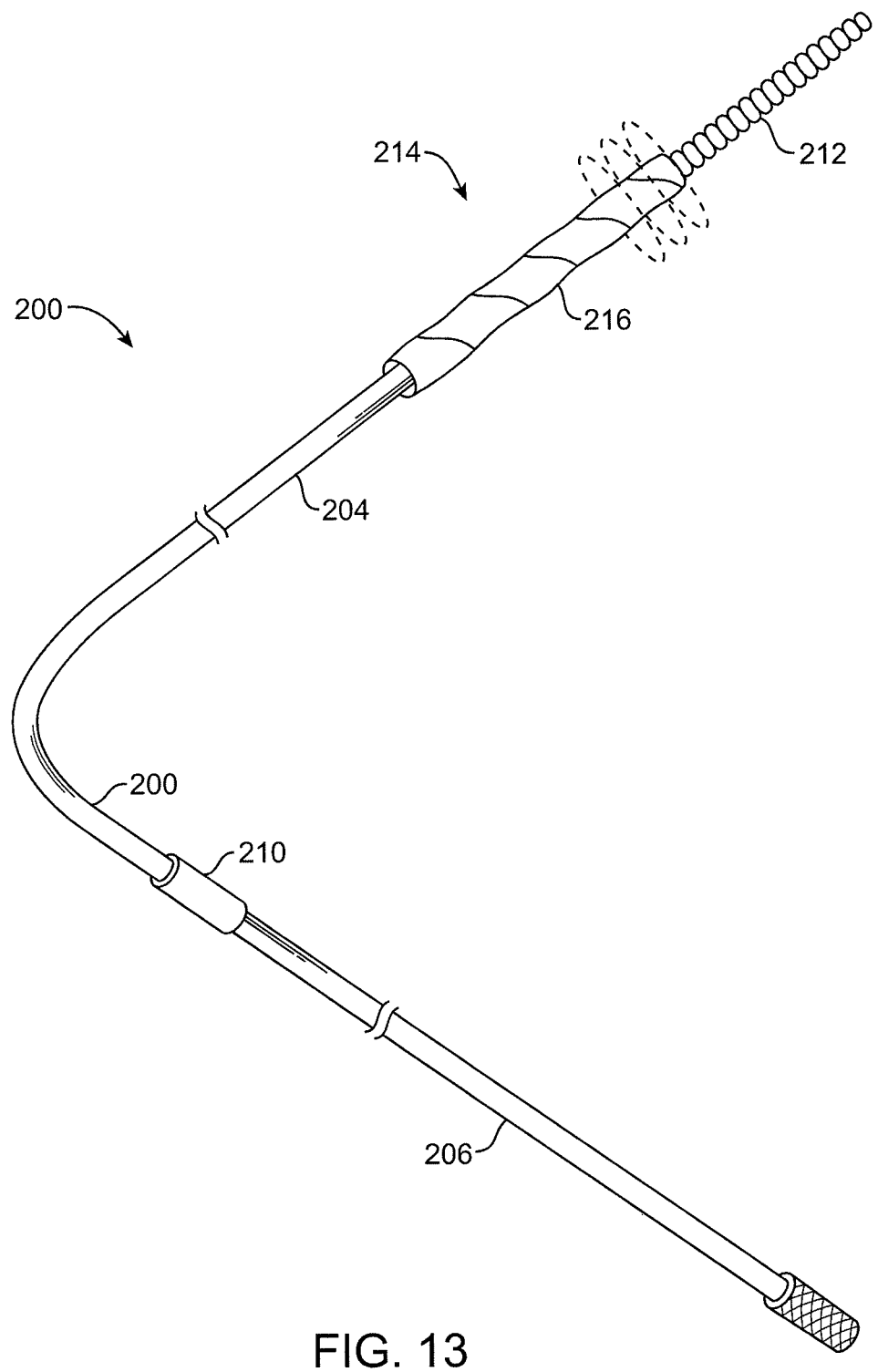
FIG. 13 illustrates a further embodiment of the decompression device of the present invention comprising a guidewire structure optimized for placing a an anchor in a ureter past a ureteral stone.

Referring now to FIG. 13, a presently preferred guidewire decompression device 200 includes a guidewire shaft 202 including a distal section 204 and a detachable proximal section 206. The guidewire shaft 202 may be formed from any conventional guidewire material, such as spring stainless steel, nitinol, other shape memory alloy, or the like. The distal section 204 and detachable proximal section 206 will be held together by a coupling member 210 which permits unscrewing or other selective detachment of the proximal section 206 from the distal section 204 after the guidewire 200 has been fully advanced into the ureter. Preferably, a proximal end of the distal section 204 will be pre-shaped so that it assumes a "pigtail" or other enlarged configuration to anchor that end within the patient's bladder after deployment.

The decompression device 200 preferably further includes a steerable distal tip 212, preferably in the form of a coil or other conventional steering element. A deployable anchor 214, typically in the form of an extendable/retractable sleeve 216 is attached near the distal end of the distal section 204, preferably immediately proximal to the steerable distal tip 212. The sleeve may be composed of any of the film or fabric materials described hereinbefore. To prevent binding prior to deployment, the sleeve will typically be tensioned or elongated, be folded or wound around the guidewire shaft, or be sufficiently thin and supple to be passively compressed to reduce the profile during delivery, thus facilitating passage beyond the stone The sleeve 216, however, will be structured and mounted so that it will compress and radially expand, as shown in broken line, when the sleeve is subsequently drawn proximally against a ureteral stone. As this embodiment may not be removed without removal of the stone, it is principally useful for pain relief prior to lithotripsy or other stone removal protocols.

Figure 14A:
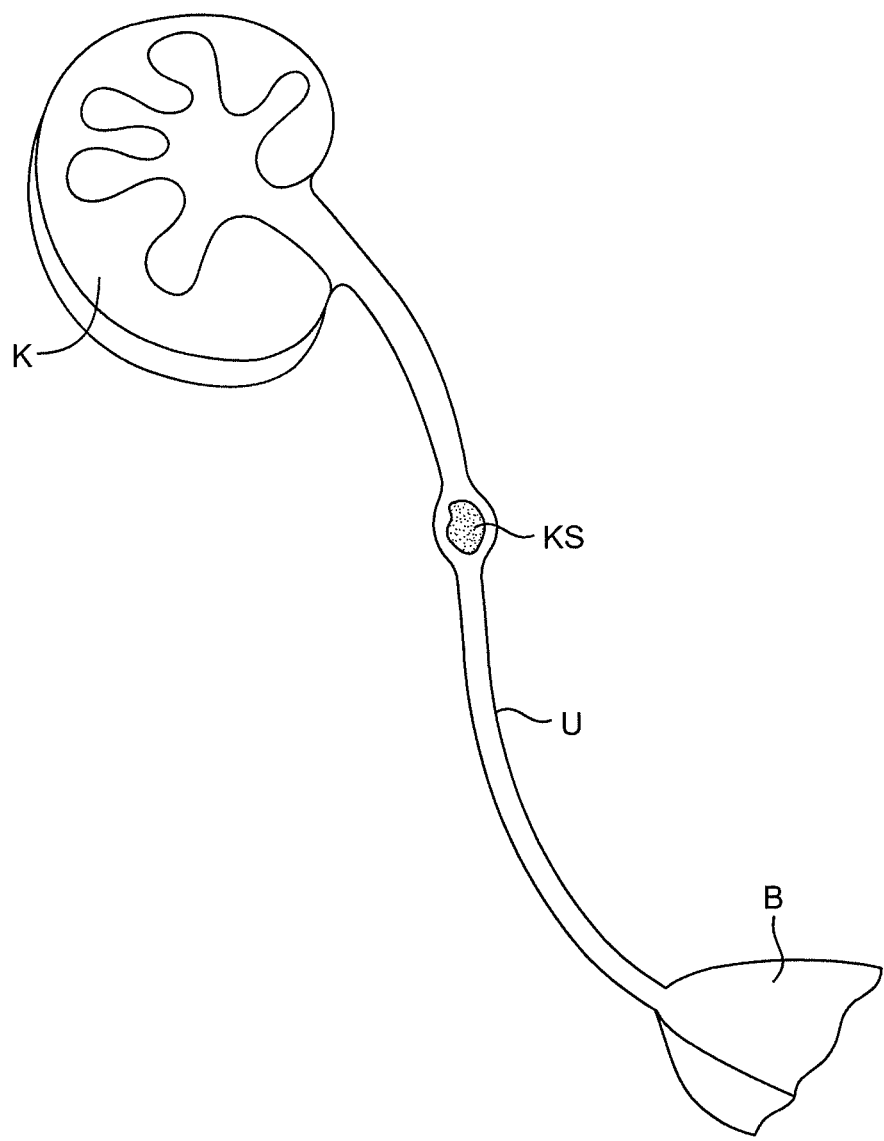
FIGS. 14A through 14E illustrate the use of the guidewire device of FIG. 13 for placing the decompression device past a ureteral stone in a patient.

Referring now to FIGS. 14A through 14E, use of the decompression device 200 will be described in more detail. As shown in FIG. 14A, a ureteral stone KS is lodged in a ureter U between the kidney K and a bladder B. Without treatment, such a lodged kidney stone KS can fully occlude the ureter, thus causing urine build-up and excessive pressure within the kidney and upper ureter.

Figure 14B:
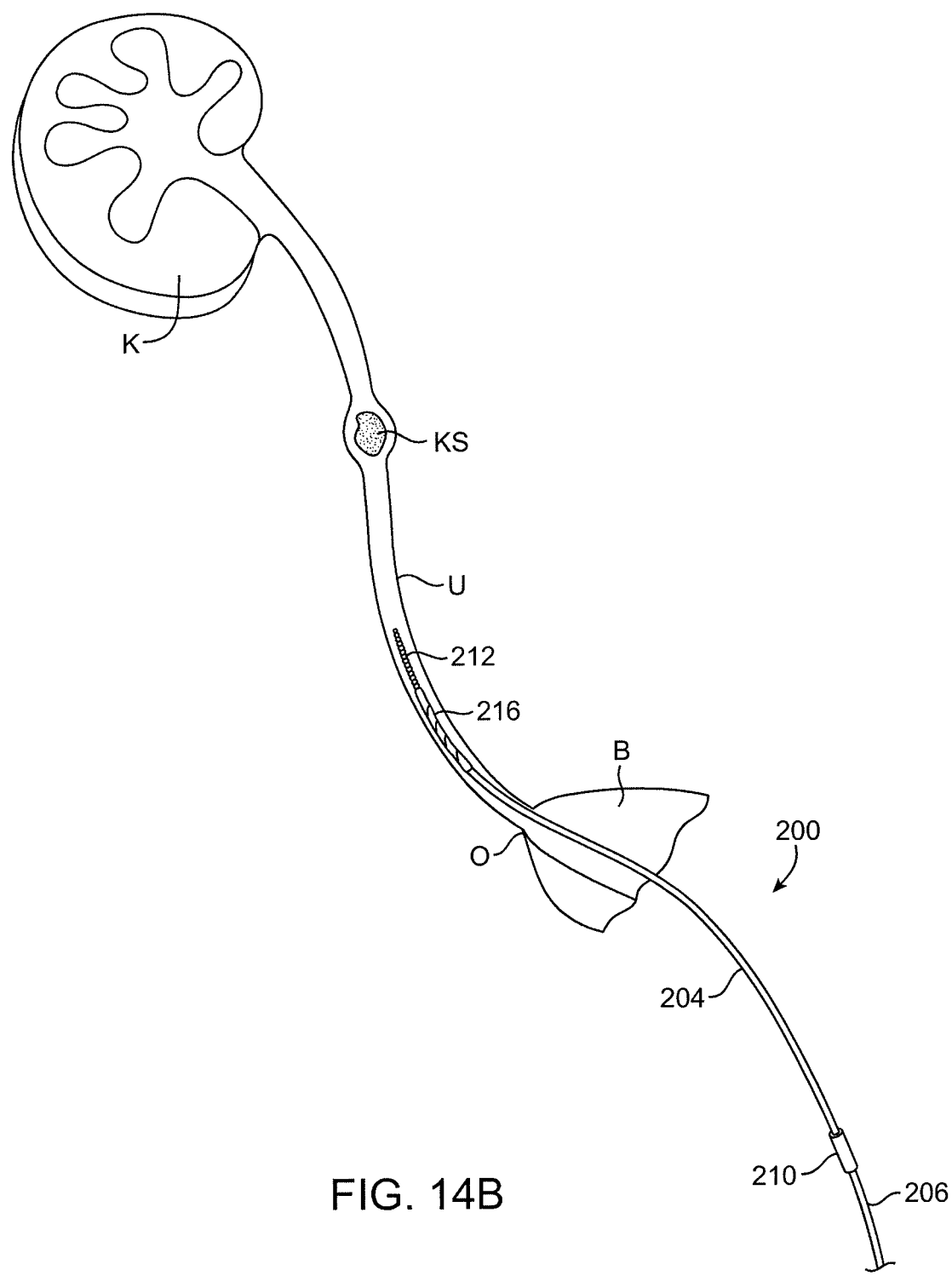
Figure 14C:
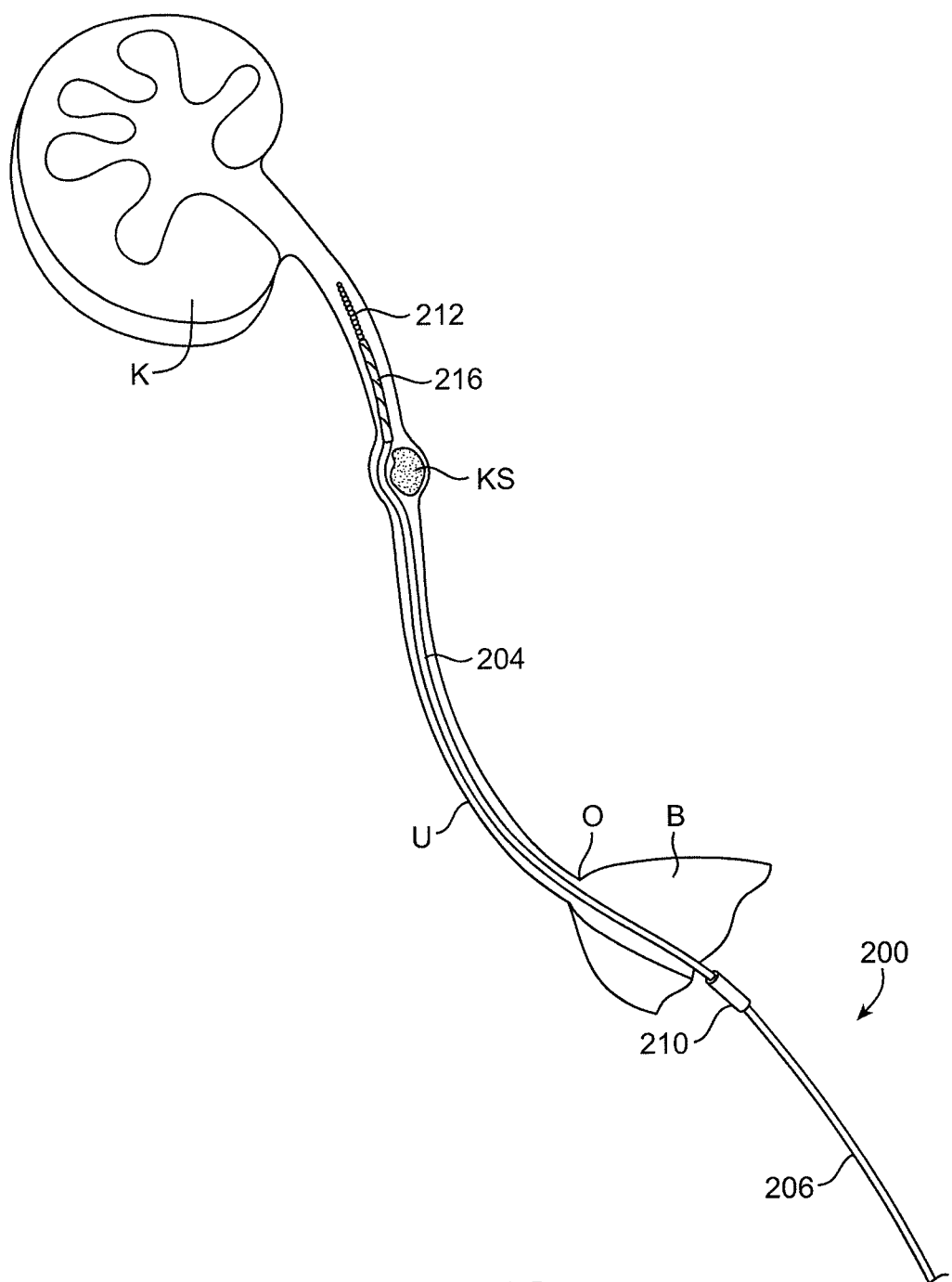

To decompress and provide leakage past the ureteral stone KS, the decompression device 200 is introduced through the patient's urethra (not shown) through the bladder B (partially shown) and finally through the os O into the ureter U, as shown in FIG. 14B. The decompression device 200 is further advanced as shown in FIG. 14C, until the sleeve is positioned just distally of the ureteral stone KS. It will be appreciated that the low-profile guidewire will be significantly easier to advance past the ureteral stone KS than some of the larger diameter tubular devices described earlier.

Figure 14D:
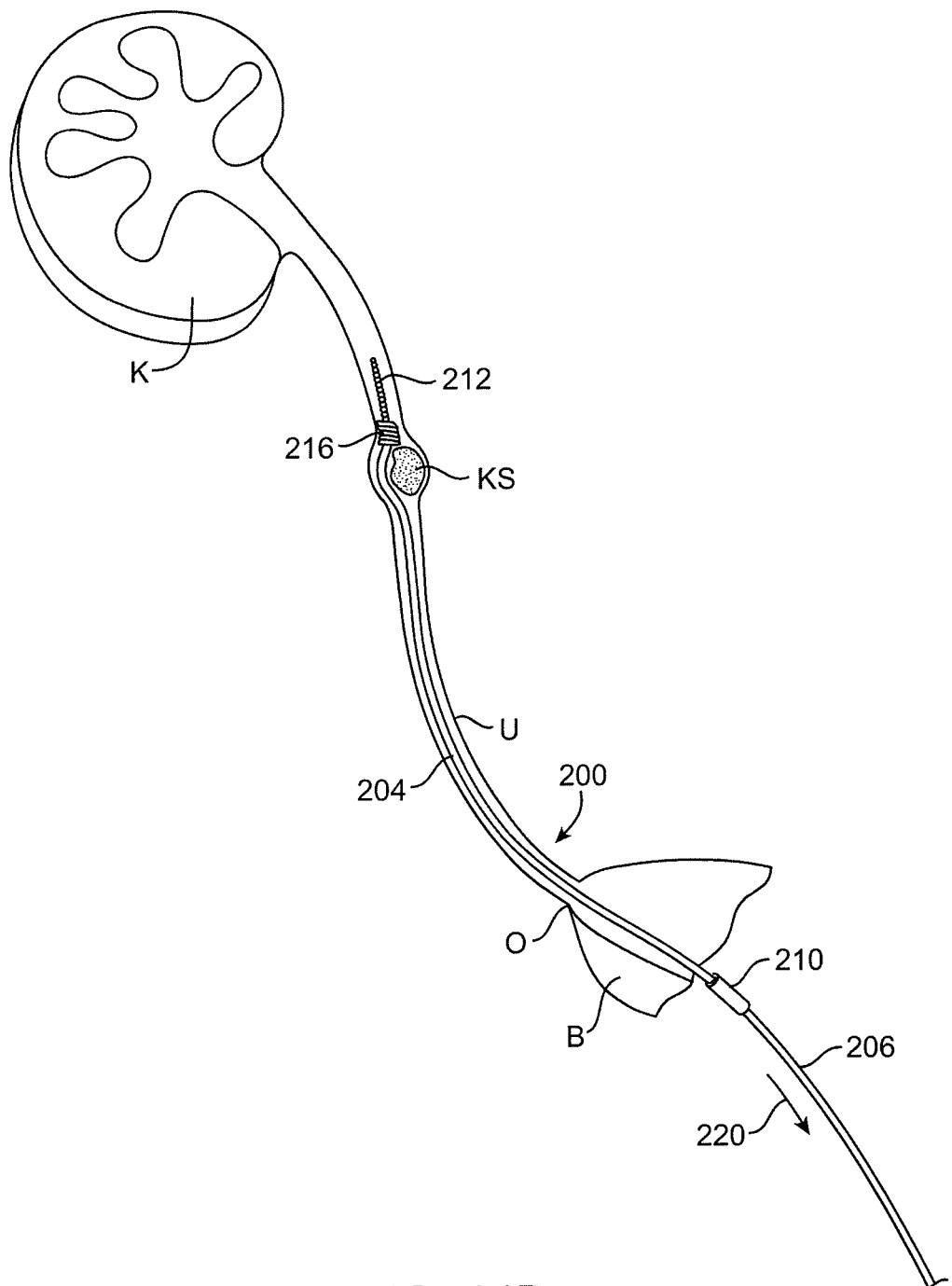
Figure 14E:
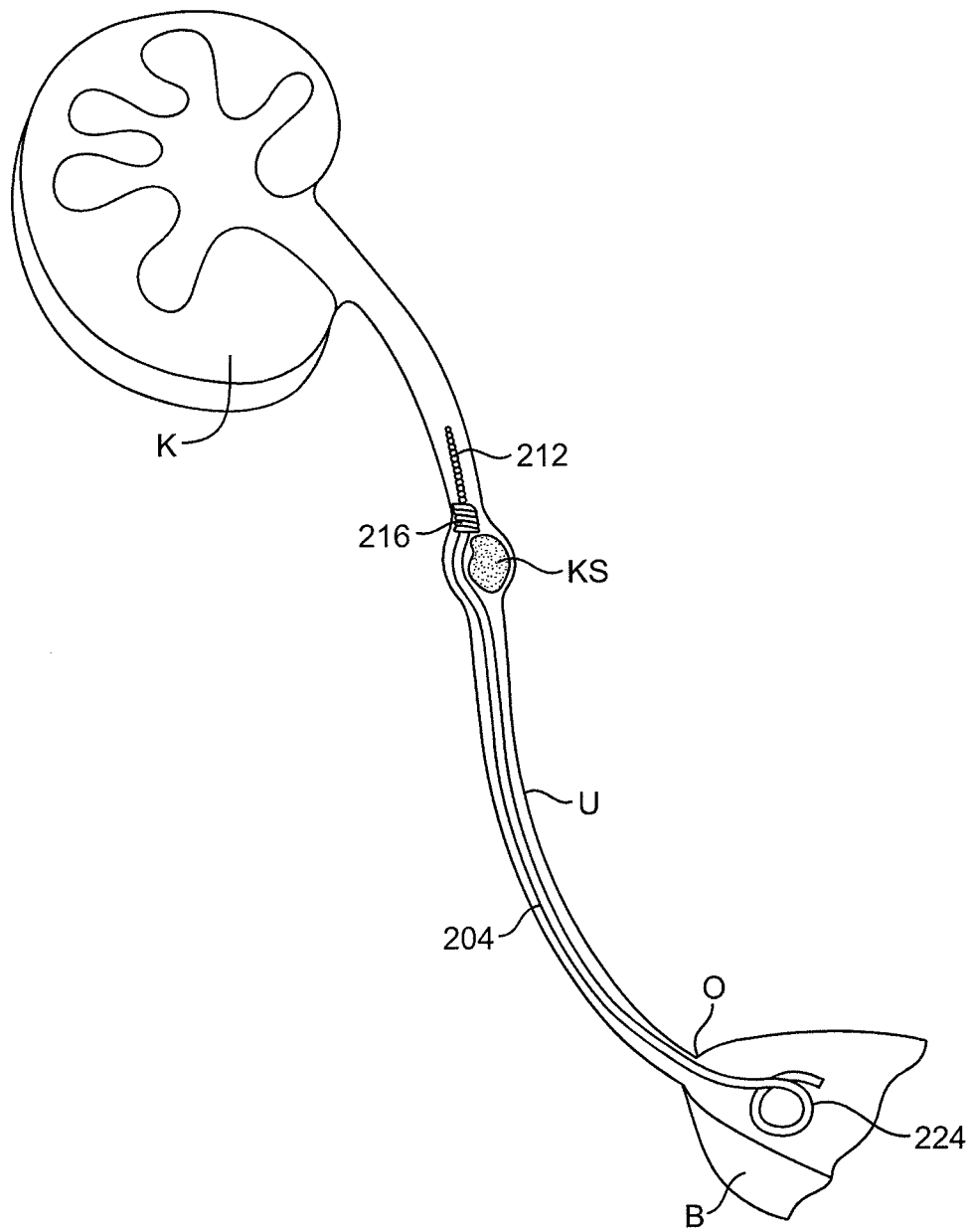

After the sleeve 216 has been advanced past the ureteral stone KS, the decompression device may be withdrawn proximally in the direction of arrow 220 in FIG. 14D. This causes the free (proximal) end of the sleeve to engage the stone and to first unfurl and subsequently compact against the distal side of the ureteral stone KS. This compaction anchors the decompression device in place within the ureter U, without the necessity of placing an anchor in the kidney, as in existing ureteral stents. The compacted sleeve 216, as with prior anchoring structures, will be adapted and formed so that it permits a variety of leakage paths through its structure, even when fully compacted above the stone in ureter or against the stone. The body of the guidewire shaft 202 will provide the desired leakage path directly past the ureteral stone KS, and may have surface details to enhance such leakage. As shown in FIG. 14E, after the distal portions of the decompression device 200 have been properly placed, the proximal section 206 of the catheter shaft 200 may be detached from the distal section, allowing the proximal end of the distal section 204 to assume a pigtail shape, as shown in 224 in Fig. E.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A device for decompressing a ureteral stone in a ureter, said device comprising:
    a guidewire having a distal tip; and
    an anchor attached to the guidewire immediately proximal to the distal tip;
    wherein the anchor is configured to compact axially and expand radially outwardly within the ureter as the anchor is drawn proximally by the guidewire;
    wherein the guidewire includes a distal section and a proximal section which is detachable from the distal section;
    wherein the expanded anchor is configured to engage and anchor against a distal side of the stone to hold the distal section of the guide member in place within the ureter when the distal section is detached from the proximal section;
    wherein a proximal portion of the distal section is configured to assume a pigtail shape after the distal section has been detached from the proximal section; and
    wherein the body of the distal section of the guide member proximal of the anchor is configured to remain between the ureteral stone and a wall of the ureter to create a leakage path past the stone.

2. A device as in claim 1, wherein the guidewire has a length in the range from 100 cm to 200 cm.

3. A device as in claim 2, wherein the guidewire comprises a distal length in the range from 20 cm to 40 cm and a separable proximal length in the range from 80 cm to 160 cm.

4. A device as in claim 1, further comprising a retrieval cord attached to the proximal end of the distal length of the guidewire.

5. A device as in claim 1, wherein the anchor comprises a tube, a strip, a sleeve, or a ribbon.

6. A device as in claim 5, wherein the anchor has a length in the range from 2 cm to 8 cm prior to deployment.

7. A device as in claim 6, wherein the anchor comprises a material selected from the group consisting of polymer films, woven fabrics, non-woven fabrics and composite and laminates thereof.

8. A device as in claim 6, wherein the anchor material is porous or perforated to promote leakage of urine therethrough when compressed.

9. A device as in claim 1, wherein the distal end of the guidewire is steerable.

10. A device as in claim 1, wherein the anchor is adapted to permit urine to flow by when the anchor is compressed.

11. A device as in claim 10, wherein the anchor is a strip with an "H"-shaped pattern or a "C"-shaped pattern so that when compressed the anchor forms bypass channels.

* * * * *